US011807858B2

(12) United States Patent
Martinell et al.

(10) Patent No.: US 11,807,858 B2
(45) Date of Patent: Nov. 7, 2023

(54) METHODS FOR PLANT TRANSFORMATION USING SPECTINOMYCIN SELECTION

(71) Applicant: Monsanto Technology LLC, St. Louis, MO (US)

(72) Inventors: Brian J. Martinell, St. Louis, MO (US); Michael W. Petersen, Sauk City, WI (US); David A. Somers, Mystic, CT (US); Yuechun Wan, Madison, WI (US); Edward Williams, Madison, WI (US); Xudong Ye, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 17/118,539

(22) Filed: Dec. 10, 2020

(65) Prior Publication Data

US 2021/0246459 A1 Aug. 12, 2021

Related U.S. Application Data

(60) Continuation of application No. 16/393,833, filed on Apr. 24, 2019, now Pat. No. 10,907,167, which is a continuation of application No. 15/638,200, filed on Jun. 29, 2017, now abandoned, which is a division of application No. 14/507,744, filed on Oct. 6, 2014, now Pat. No. 9,714,428, which is a division of application No. 13/899,452, filed on May 21, 2013, now Pat. No. 8,872,000, which is a division of application No. 13/213,021, filed on Aug. 18, 2011, now Pat. No. 8,466,345, which is a division of application No. 12/045,562, filed on Mar. 10, 2008, now Pat. No. 8,030,544.

(60) Provisional application No. 60/915,066, filed on Apr. 30, 2007, provisional application No. 60/894,096, filed on Mar. 9, 2007.

(51) Int. Cl.
*C12N 15/82* (2006.01)
*C12N 5/00* (2006.01)
*A01H 4/00* (2006.01)
*C12N 5/04* (2006.01)
*G01N 33/00* (2006.01)
*C12N 9/10* (2006.01)
*A01H 6/20* (2018.01)
*A01H 6/54* (2018.01)
*A01H 6/46* (2018.01)
*A01H 6/60* (2018.01)
*C12N 1/20* (2006.01)
*C12R 1/41* (2006.01)

(52) U.S. Cl.
CPC ......... *C12N 15/8209* (2013.01); *A01H 4/003* (2013.01); *A01H 4/008* (2013.01); *C12N 5/0025* (2013.01); *C12N 5/04* (2013.01); *C12N 9/1029* (2013.01); *C12N 15/8201* (2013.01); *C12N 15/8202* (2013.01); *C12N 15/8205* (2013.01); *C12N 15/8221* (2013.01); *C12N 15/8265* (2013.01); *C12N 15/8271* (2013.01); *C12N 15/8274* (2013.01); *C12N 15/8275* (2013.01); *C12N 15/8277* (2013.01); *C12N 15/8281* (2013.01); *G01N 33/0098* (2013.01); *A01H 6/202* (2018.05); *A01H 6/4684* (2018.05); *A01H 6/542* (2018.05); *A01H 6/604* (2018.05); *C12N 1/205* (2021.05); *C12N 15/8261* (2013.01); *C12R 2001/41* (2021.05); *C12Y 203/01081* (2013.01)

(58) Field of Classification Search
CPC .................................................. C12N 15/8209
See application file for complete search history.

(56) References Cited

U.S. PATENT DOCUMENTS

| | | | |
|---|---|---|---|
| 3,068,142 A | 12/1962 | Bader et al. | |
| 5,073,675 A | 12/1991 | Jones et al. | |
| 5,217,902 A * | 6/1993 | Jones | C12N 9/12 435/15 |
| 5,262,316 A | 11/1993 | Engler et al. | |
| 5,286,635 A | 2/1994 | Hanson et al. | |
| 5,567,599 A | 10/1996 | Lemieux | |
| 5,576,203 A | 11/1996 | Hoffman | |
| 5,698,425 A | 12/1997 | Ligon et al. | |
| 5,736,369 A | 4/1998 | Bowen | |
| 6,127,181 A * | 10/2000 | Kadkade | A01N 3/00 435/1.3 |
| 6,140,555 A | 10/2000 | Reichert et al. | |

(Continued)

FOREIGN PATENT DOCUMENTS

| | | |
|---|---|---|
| BR | 9712695 | 10/1999 |
| CN | 1597969 A | 3/2005 |

(Continued)

OTHER PUBLICATIONS

Bechtold et al., "The maternal chromosome set is the target of the T-DNA in the planta transformation of *arabidopsis thaliana*," *Genetics Society of America*, 155(4):1875-1887, 2000.

(Continued)

*Primary Examiner* — Susan McCormick Ewoldt
(74) *Attorney, Agent, or Firm* — DENTONS US LLP; Paula DeGrandis

(57) ABSTRACT

The present invention relates to methods and compositions for transforming soybean, corn, cotton, or canola explants using spectinomycin as a selective agent for transformation of the explants. The method may further comprise treatment of the explants with cytokinin during the transformation and regeneration process.

22 Claims, 6 Drawing Sheets

Specification includes a Sequence Listing.

(56) References Cited

U.S. PATENT DOCUMENTS

| | | | |
|---|---|---|---|
| 6,153,813 A | 11/2000 | Reichert et al. | |
| 6,307,127 B1 | 10/2001 | Jorsboe et al. | |
| 6,603,061 B1* | 8/2003 | Armstrong | C12N 15/8205 435/426 |
| 6,900,057 B2 | 5/2005 | Burns et al. | |
| 7,279,336 B2 | 10/2007 | Gelvin et al. | |
| 7,288,694 B2 | 10/2007 | Armstrong et al. | |
| 7,402,734 B2 | 7/2008 | Martinell et al. | |
| 7,601,889 B2 | 10/2009 | Napier et al. | |
| 8,030,544 B2 | 10/2011 | Martinell et al. | |
| 8,044,260 B2 | 10/2011 | Dersch et al. | |
| 8,362,317 B2 | 1/2013 | Calabotta et al. | |
| 8,466,345 B2 | 6/2013 | Martinell et al. | |
| 2003/0074686 A1 | 4/2003 | Heinz et al. | |
| 2004/0034889 A1 | 2/2004 | Khan | |
| 2004/0210958 A1* | 10/2004 | Duncan | A01H 4/005 800/278 |
| 2005/0044595 A1 | 2/2005 | Arias et al. | |
| 2006/0059589 A1* | 3/2006 | Martinell | C12N 15/8205 800/312 |
| 2006/0260012 A1 | 11/2006 | Khan | |
| 2007/0039075 A1 | 2/2007 | Tissot et al. | |

FOREIGN PATENT DOCUMENTS

| | | |
|---|---|---|
| CN | 1681923 A | 10/2005 |
| CN | 1685047 A | 10/2005 |
| EP | 0430511 | 6/1991 |
| EP | 1 236 801 | 9/2002 |
| WO | WO 98/20144 | 5/1998 |
| WO | WO 99/10513 | 3/1999 |
| WO | WO 00/42207 | 7/2000 |
| WO | WO 01/29241 | 4/2001 |
| WO | WO 02/066599 | 8/2002 |
| WO | WO 03/017752 | 3/2003 |
| WO | WO 03/100381 | 12/2003 |
| WO | WO 2004/000006 | 12/2003 |
| WO | WO 2004/009761 | 1/2004 |
| WO | WO 2004/029256 | 4/2004 |
| WO | WO 2004/078935 | 9/2004 |
| WO | WO 2005/122750 | 12/2005 |
| WO | WO 2006/026466 | 3/2006 |
| WO | WO 2007/079538 | 7/2007 |
| WO | WO 2007/103769 | 9/2007 |

OTHER PUBLICATIONS

Bito et al., "Revised Analysis of aadA2 Gene of Plasmid pSa," *Antimicrobial Agents and Chemotherapy* 38(5) 1172-1175; 1994.

Bouchez et al., "A binary vector based on basta resistance for in planta transformation of *arabidopsis thaliana*," *C.R. Acad. Sci. Paris*, 316:1188-1193, 1993.

Bretagne-Sagnard et al., "Selection of transgenic flax plants is facilitated by spectinomycin," *Transgenic Res.*, 5:131-137, 1996.

Chai et al., "Optimum moisture contents of seeds stored at ambient temperatures," *Seed Science Research*, 8(Supplement 1):23-28, 1998.

Chen, Database WPI Week 200432, Oct. 21, 2003.

Finer et al., "Transformation of soybean via particle bombardment of embryogenic suspension culture tissue," *In Vitro Cell. Dev. Biol.*, 27P:175-182, 1991.

Francois et al., "Different approaches for multi-transgene-stacking in plants," *Plant Science*, 163:281-295, 2002.

Hewezi et al., "Dehydrating immature embryo split apices and rehydrating with agrobacterium tumefaciens: a new method for genetically transforming recalcitrant sunflower," *Plant Mol. Biol. Reporter*, 20:335-345, 2002.

Hincee et al., "Production of transgenic soybean plants using agrobacterium-mediated DNA transfer," *Bio/Technology*, 6:915-922, 1988.

Jones et al., "Effective vectors for transformation, expression of heterologous genes, and assaying transposon excision in transgenic plants," *Transgenic Res.*, 1:285-297, 1992.

Kofer et al., "PEG-mediated plastid transformation in higher plants," *In Vitro Cell Dev. Bio.—Plants*, 34:303-309, 1998.

Krysan, "Ice-Cap. A high-throughput method for capturing plant tissue samples for genotype analysis," Plant Physiology, 135:1162-1169, 2004.

Kumar et al., "Stable transformation of the cotton plastid genome and maternal inheritance of transgenes," Plant Mol. Biol., 58:203-216, 2004.

Kumar et al., Poster: Emerging technologies: Engineering the cotton chloroplast genome and maternal inheritance of transgenes—Abstract #905, 2004 Annual Meeting of the American Society of Plant Biologists, https://abstracts.aspb.org/pb2004/public/P72/7106.html retrieved Dec. 20, 2011.

Lacorte et al., "Transient expression of GUS and the 2S albumin gene from Brazil nut in peanut (*arachis hypogaea L.*) seed explants using particles bombardment," *Plant Cell Reports*, 16:619-623, 1997.

Larkin et al., "Transgenic white clover. Studies with the auxin-responsive promoter, GH3, in root gravitropism and lateral root development," *Transgenic Research*, 5:3235-335, 1996.

Lim et al., "Construction of small binary vectors for agrobacterium-mediated transformation in plants," *J. of Plant Biol.*, 42(4):317-320, 1999.

Lim et al., "Expression of the glutathione S-transferase gene (NT107) in transgenic dianthus superbus," *Plant Cell, Tissue and Organ Culture*, 80:277-286, 2005.

Maliga, "Plastid Transformation in Higher Plants," Ann. Rev. Plant Biol., 55:289-313, 2004.

McCabe et al., "Stable transformation of soybean (*Glycine max*) by particle acceleration," *Bio/Technology*, 6:923-926, 1988.

Oreifig et al., "Development of a non-lethal selection system by using the aadA marker gene for efficient recovery of transgenic rice (*Oryza sativa L.*)" *Plant Cell Reports*, 22:490-496, 2004.

Patnaik et al., "Agrobacterium-mediated transformation of mature embryos of triticum aestivum and triticum durum," *Curr. Sci.*, 91(3):307-317, 2006.

Paz et al., "Improved cotyledonary node method using an alternative explant derived from mature seed for efficient agrobacterium-mediated soybean transformation," *Plant Cell Rep.*, 25:206-213, 2006.

Popelka et al., "Genetic transformation of cowpea (*vigna unguiculata L.*) and stable transmission of the transgenes to progeny," *Plant Cell Rep.*, 25:304-312, 2006.

Pyke et al., "Marking cell layers with spectinomycin provides a new tool for monitoring cell fate during lead development," *J. Experimental Botany*, 51(351):1713-1720, 2000.

Rohini et al., "Transformation of peanut (*arachis hypogaea L.*): a non-tissue culture based approach for generating transgenic plants," *Plant Sci.*, 150:41-49, 2000.

Sandvang, "Novel streptomycin and spectinomycin resistance gene as a gene cassette within a class 1 integron isolated from *escherichia coli*," *Antimicrobial Agents and Chemotherapy*, 43(12):3036-3038, 1999.

Schnug et al., "Preparation techniques of small sample sizes for sulphur and indirect total glucosinolate analysis in *brassica* seeds by X-Ray fluorescence spectroscopy," *Fett Sci. Technol.*, 95(9):334-337, 1993.

Schroder et al., "Transformation of *brassica napus* by using the aadA gene as slectable marker and inheritance studies of the marker genes," *Physiologia Plantarum*, 92:37-46, 1994.

Senaratna et al., "Dehydration injury in germinating soybean (*glycine max*L. merr.) seeds," *Plant Physiol.*, 72:620-624, 1983.

Simoens et al., "A binary vector for transferring genomic libraries to plants," *Nucleic Acids Research*, 14(20):8073-8090, 1998.

Svab et al., "Aminoglycoside-3"-adenyltransferase confers resistance to spectinomycin and treptomycin in nicotiana tabacum," *Plant Mol. Biol.* 14:197-205, 1990.

Svab et al., "High-frequency plastid transformation in tobacco by selection for a chimeric aadA gene," *Proc. Natl. Acad. Sci. USA*, 90:913-917, 1993.

Trick et al., "SAAT: sonication-assisted agrobacterium-mediated transformation," *Transfenic Research*, 6:329-336, 1997.

(56) References Cited

OTHER PUBLICATIONS

Vertucci et al., "Theoretical basis of protocols for seed storage," *Plant Physiol.*, 94:1019-1023, 1990.
Von Post et al., "A high-throughput DNA extraction method for barley seed," *Euphytica*, 130-255-260, 2003.
Wang et al., "Maize (*zea mays*) genetic transformation by co-cultivating germinating seed with agrobacterium tumefaciens," *Biotechnol. Appl. Biochem.*, 46:51-55, 2007.
Official Action dated Jul. 20, 2011 in Chinese Application No. 200880012913.8.
English Translation of Office Action regarding Brazilian Application No. PI 0808665-6, dated Jun. 30, 2017.
Barros et al., "Transformacao Genetica de Coffea arabica Atraves de Bombardeamento," Biotechnologia pp. 150-152, 2000.
Scofield et al., "Chloroplast targeting of spectinomycin adenyltransferase provides a cell-autonomous marker for monitoring transposon excision in tomato and tobacco," Mol. Gen. Genet. 244:189-196, 1994.
Hajdukiewicz et al. Plant Molecular Biology 25: 989-994 (1994).
Taylor et al. Journal of Bacteriology 137(1): 92-104 (1979).
Robertson, J. (2000) How to convert microeinsteins to lux. www.madsci.org/posts/archives/2000-08/965136947.Ph.r.html.

* cited by examiner

```
                        SEQUENCE LISTING

<160> NUMBER OF SEQ ID NOS: 3

<210> SEQ ID NO 1
<211> LENGTH: 792
<212> TYPE: DNA
<213> ORGANISM: Shigella sp.

<400> SEQUENCE: 1 atggggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc cacacagtga tattgatttg ctggttacgg tgaccgtaag gcttgatgaa     180
acaacgcggc gagctttgat caacgacctt ttggaaactt cggcttcccc tggagagagc     240
gagattctcc gcgctgtaga agtcaccatt gttgtgcacg acgacatcat tccgtggcgt     300
tatccagcta agcgcgaact gcaatttgga gaatggcagc gcaatgacat tcttgcaggt     360
atcttcgagc cagccacgat cgacattgat ctggctatct tgctgacaaa agcaagagaa     420
catagcgttg ccttggtagg tccagcggcg gaggaactct ttgatccggt tcctgaacag     480
gatctatttg aggcgctaaa tgaaaccta acgctatgga actcgccgcc cgactgggct      540
ggcgatgagc gaaatgtagt gcttacgttg tcccgcattt ggtacagcgc agtaaccggc     600
aaaatcgcgc cgaaggatgt cgctgccgac tgggcaatgg agcgcctgcc ggcccagtat     660
cagcccgtca tacttgaagc tagacaggct tatcttggac aagaagaaga tcgcttggcc     720
tcgcgcgcag atcagttgga agaatttgtc cactacgtga aaggcgagat caccaaggta     780
```

-continued

```
gtcggcaaat aa                                                      792

<210> SEQ ID NO 2
<211> LENGTH: 1020
<212> TYPE: DNA
<213> ORGANISM: Artificial sequence
<220> FEATURE:
<223> OTHER INFORMATION: Synthetic

<400> SEQUENCE: 2
atggcgcaag ttagcagaat ctgcaatggt gtgcagaacc catctcttat ctccaatctc    60
tcgaaatcca gtcaacgcaa atctcccta tcggtttctc tgaagacgca gcagcatcca   120
cgagcttatc cgatttcgtc gtcgtgggga ttgaagaaga gtgggatgac gttaattggc   180
tctgagcttc gtcctcttaa ggtcatgtct tctgtttcca cggcgtgcat ggggaagcg    240 gtgatcgccg aagtatcgac tcaactatca gaggtagttg gcgtcatcga gcgccatctc   300
gaaccgacgt tgctggccgt acatttgtac ggctccgcag tggatggcgg cctgaagcca   360
cacagtgata ttgatttgct ggttacggtg accgtaaggc ttgatgaaac aacgcggcga   420
gctttgatca acgacctttt ggaaacttcg gcttcccctg gagagagcga gattctccgc   480
gctgtagaag tcaccattgt tgtgcacgac gacatcattc cgtggcgtta ccagctaag    540 cgcgaactgc aatttggaga atggcagcgc aatgacattc ttgcaggtat cttcgagcca   600
gccacgatcg acattgatct ggctatcttg ctgacaaaag caagagaaca tagcgttgcc   660
ttggtaggtc cagcggcgga ggaactcttt gatccggttc ctgaacagga tctatttgag   720
gcgctaaatg aaaccttaac gctatggaac tcgccgcccg actgggctgg cgatgagcga   780
aatgtagtgc ttacgttgtc ccgcatttgg tacagcgcag taaccggcaa aatcgcgccg   840
aaggatgtcg ctgccgactg gcaatggag cgcctgccgg cccagtatca gcccgtcata   900
cttgaagcta gacaggctta tcttggacaa gaagaagatc gcttggcctc gcgcgcagat   960
cagttggaag aatttgtcca ctacgtgaaa ggcgagatca ccaaggtagt cggcaaataa  1020

<210> SEQ ID NO 3
<211> LENGTH: 227
<212> TYPE: DNA
<213> ORGANISM: Artificial sequence
<220> FEATURE:
<223> OTHER INFORMATION: Synthetic

<400> SEQUENCE: 3
gtctgttttt tgacaattga atatgagaag aaagagaaac gtgggcggcg aagctagctt    60
gcgggacctg gagagatttg ggtcctagtg aatagacttt gacggtcacg ttttaatgag   120
acaacaccaa tttcgcgagc agagatgctt gttgagattg atgtgagttc tcgtcgattc   180
agaataacgt gacaatagtc aatgattgaa ggagaaacaa agccatg                 227
```

METHODS FOR PLANT TRANSFORMATION USING SPECTINOMYCIN SELECTION

This application is a continuation of U.S. Ser. No. 16/393,833, filed Apr. 24, 2019, which is a continuation of U.S. Ser. No. 15/638,200, filed Jun. 29, 2017, now abandoned, which is a divisional of U.S. Ser. No. 14/507,744, filed Oct. 6, 2014, now U.S. Pat. No. 9,714,428, which is a divisional of U.S. Ser. No. 13/899,452, filed May 21, 2013, now U.S. Pat. No. 8,872,000, which application is a divisional of U.S. Ser. No. 13/213,021, filed Aug. 18, 2011, now U.S. Pat. No. 8,466,345, which application is a divisional of U.S. application Ser. No. 12/045,562, filed Mar. 10, 2008, now U.S. Pat. No. 8,030,544, which application claims the priority of U.S. Provisional application Ser. No. 60/894,096, filed Mar. 9, 2007, and 60/915,066, filed Apr. 30, 2007, the entire disclosures of which are incorporated herein by reference in their entirety.

BACKGROUND OF THE INVENTION

1. Field of the Invention

The invention relates generally to methods for preparing and transforming meristematic plant tissue and selection and subsequent regeneration of transgenic plants.

2. Description of Related Art

Transformed plants may be obtained by directly treating meristematic tissue of a plant embryo. The meristematic tissue contains formative plant cells that differentiate to produce multiple plant structures including stem, roots, leaves, germ line tissue, and seeds. The meristematic tissue, such as soybean tissue, may be excised from seeds. Methods of genetically transforming soybeans (*Glycine max*) using bacterially-mediated gene transfer directly on the meristematic cells of soybean embryos are known. Isolated cotton meristems and shoot apex tissues have been transformed. Use of a cytokinin to induce shoot development in tissue culture has been reported.

A number of selective agents are known for use in methods for genetically transforming plant cells. An aminoglycoside-3'-adenyltransferase has been used as a selectable marker in transforming plant cells. Fusion of aadA with a chloroplast transit peptide-encoding sequence, to allow for directing a nuclear produced AadA to the chloroplast, has not been reported.

SUMMARY OF THE INVENTION

In one aspect, the invention provides a method for producing a transgenic plant containing at least two heterologous nucleic acid sequences comprising: (a) providing an explant comprising a first heterologous nucleic acid sequence that confers resistance to a herbicide; (b) transforming the explant to comprise a second heterologous nucleic acid sequence comprising a selectable marker gene conferring spectinomycin resistance; and (c) regenerating an explant that exhibits spectinomycin resistance into a transgenic plant containing at least two heterologous nucleic acid sequences. In one embodiment, the explant comprises an embryonic meristem. In another embodiment, the first heterologous nucleic acid sequence confers resistance to glyphosate, bialaphos, phosphinothricin, Basta, glufosinate, 2,4-D, kanamycin and related aminoglycosides, hygromycin, an acetyl-coA carboxylase inhibitor, an oxygen radical generator, or dicamba. In another embodiment, the explant is a soybean, corn, cotton, or canola explant. In a particular embodiment, the explant is a soybean or cotton explant, such as a soybean plant.

In another aspect, the invention provides a method of producing a transgenic plant comprising: (a) transforming at least a first seed explant with a heterologous nucleic acid sequence comprising a selectable marker conferring tolerance to spectinomycin; and (b) regenerating a transgenic plant from the transformed cells, wherein the explant is contacted, prior to, concurrently with, and/or following step (a) or step (b), with at least a first media comprising spectinomycin to select transformed cells comprising said selectable marker. In one embodiment, the transgenic plant arises from transformation of a meristem that results in transformation of germline tissue. In certain embodiments, the resulting plant is non-chimeric. In yet other embodiments, the resulting plant is chimeric. In a particular embodiment, at least one shoot of the resulting plant is transgenic and is non-chimeric. In another particular embodiment, at least one shoot of the resulting plant is transgenic and non-chimeric while at least one other shoot or one other root does not comprise a sequence comprised on the heterologous nucleic acid. In certain embodiments, the first seed explant comprises a transgene. In other embodiments, the explant comprises an embryonic meristem. In yet other embodiments, during or following step (a), explants are grown in the presence of a selective agent at 35° C.-40° C. and/or are grown under lighting conditions that allow for normal plastid development. In still yet other embodiments, growth at 35°-40° C. is performed for 1-7 days or the lighting conditions comprise at least 5 µEinsteins with about a 16 hour light/8 dark photoperiod.

In some embodiments, the explant is stored at a temperature of between 0-15° C. for between 1 hour and 7 days prior to step (a). In other embodiments, the media comprises from about 15 mg/L to about 1500 mg/L spectinomycin. The invention further relates to a method wherein the cells of the explant comprise a coding sequence conferring tolerance to glyphosate, bialaphos, phosphinothricin, Basta, glufosinate, 2,4-D, kanamycin and related aminoglycosides, hygromycin, streptomycin, ampicillin, or dicamba. In some embodiments, step (a) comprises growing an explant on a co-culture medium comprising spectinomycin. In other embodiments the explant is not contacted with a medium comprising spectinomycin after being transferred from a co-culture medium. Alternatively, in other embodiments the explant is contacted with a medium comprising spectinomycin after being transferred from a co-culture medium. In some embodiments the explant that is regenerating into a plant is transferred to soil or soil substitute for rooting without pre-rooting in aseptic media. In other embodiments, the heterologous nucleic acid further comprises a coding sequence that confers a trait of agronomic interest or improved end use.

In other embodiments, the invention provides a method of producing a transgenic plant comprising: (a) transforming at least a first seed explant with a heterologous nucleic acid sequence comprising a selectable marker conferring tolerance to spectinomycin; and (b) regenerating a transgenic plant from the transformed cells, wherein the explant is contacted, prior to, concurrently with, and/or following step (a) or step (b), with at least a first media comprising spectinomycin to select transformed cells comprising said selectable marker, wherein step (a) comprises transforming the cell of the explant with at least a second heterologous nucleic acid. In particular embodiments, the second heterologous nucleic acid comprises a coding sequence that confers herbicide tolerance. In certain embodiments, the first and second heterologous nucleic acids are integrated at different loci within the genome of the cell. Certain embodiments of the invention comprise, prior to step (a), the step of priming the seed, wherein the priming comprises contacting the seed with a cytokinin. In other embodiments a method further comprising contacting the explant with a cytokinin prior to, concurrently with and/or following step (b) is contemplated. In particular embodiments, the cytokinin is selected from the group consisting of thidiazuron, BAP (6-Benzylaminopurine), kinetin, CPPU (N-(2-Chloro-4-pyridyl)-N'-phenylurea), 2iP (6-(y,y-Dimethylallylamino)purine), Zeatin, Zeatin-riboside, Adenine, and TIBA (2,3,5-Triiodobenzoic acid).

In some embodiments, step (a) comprises contacting the explant with recombinant Rhizobiaceae comprising said heterologous nucleic acid, wherein the Rhizobiaceae have been exposed to thidiazuron prior to or concurrently with contacting the explant with the recombinant Rhizobiaceae. In certain embodiments the Rhizobiaceae is exposed to thidiazuron for from about 1 to 5 days prior to contacting the explant with the recombinant Rhizobiaceae. In other embodiments, the Rhizobiaceae are suspended in the presence of a selective agent active against an untransformed explant prior to contacting the explants with the Rhizobiaceae. In certain embodiments, the Rhizobiaceae are selected from the group consisting of: Agrobacteria, Sinorhizobia, Mesorhizobia, and Rhizobia. In yet other embodiments, the explants are grown in the presence of a fungicide prior to, during, or subsequent to the step of transforming at least a first seed explant with a heterologous nucleic acid sequence comprising a selectable marker conferring tolerance to spectinomycin. In certain embodiments, the explants are grown in the presence of a fungicide and DMSO. In particular embodiments, the explants are grown in the presence of nystatin, thiabendazole, and DMSO.

In certain embodiments the explant is a soybean, corn, cotton, or canola explant. In particular embodiments the explant is a soybean explant or a cotton explant.

In certain embodiments the method of: producing a transgenic plant comprising: (a) transforming at least a first seed explant with a heterologous nucleic acid sequence comprising a selectable marker conferring tolerance to spectinomycin; and (b) regenerating a transgenic plant from the transformed cells, wherein the explant is contacted, prior to, concurrently with, and/or following step (a) or step (b), with at least a first media comprising spectinomycin to select transformed cells comprising said selectable marker, further comprises the step of (c) obtaining a progeny plant of any generation of the transgenic plant that comprises the gene conferring the trait of interest and lacks the selectable marker. In certain embodiments, the heterologous nucleic acid comprises a first DNA segment comprising left and right T-DNA borders flanking a gene conferring a trait of interest; and a second DNA segment comprising a second set of left and right T-DNA borders flanking said selectable marker conferring tolerance to spectinomycin. In other embodiments, the method further comprises the step of (c) obtaining a progeny plant of any generation of the transgenic plant that comprises the gene conferring the trait of interest and lacks the selectable marker.

In some embodiments, the heterologous nucleic acid comprises right and left T-DNA borders and first and second DNA segments, wherein the first DNA segment comprises a gene of interest located after the right border, and wherein the second DNA segment comprises the selectable marker located after the left border. In certain embodiments, the heterologous nucleic acid comprises first and second right T-DNA borders, wherein a first DNA segment comprising a gene of interest is located after the first right border and a second DNA segment comprising the selectable marker is located after the second right border.

In certain embodiments, the method comprises culturing said explant on media lacking spectinomycin for from about 1 to about 7 days during step (b). In other embodiments, the method comprises contacting the explant with at least a first media comprising spectinomycin is for from about 15 minutes to about 7 days. In particular embodiments, the selectable marker is encoded by aadA. In more particular embodiments, aadA comprises SEQ ID NO: 1. In certain embodiments, the aadA gene is fused to a chloroplast transit peptide. In particular embodiments, aadA comprises SEQ ID NO:2.

In certain embodiments, the explant is further defined as having been maintained prior to step (b) under conditions wherein the explant does not germinate and remains viable and competent for genetic transformation. In some embodiments said conditions comprise dehydrating the explant or a seed comprising the explant. In certain embodiments, the method is further defined as comprising increasing the moisture content of the explant prior to or concurrently with step (b). In particular embodiments, said conditions comprise an internal moisture content of the explant of from about 3% to about 25%. In more particular embodiments, said conditions comprise an internal moisture content of the explant of from about 3% to about 16%. In some embodiments said conditions comprise maintaining the explant at a temperature of between about −80° C. and about 60° C.

In some embodiments, the method comprises priming the explant prior to step (b). In particular embodiments, priming the seed comprises contacting the explant or a seed comprising the explant with an aqueous solution comprising water, a plant growth regulator, a selection agent, or a cell membrane conditioner.

In certain embodiments comprising the method of producing a transgenic plant comprising: (a) transforming at least a first seed explant with a heterologous nucleic acid sequence comprising a selectable marker conferring tolerance to spectinomycin; and (b) regenerating a transgenic plant from the transformed cells, wherein the explant is contacted, prior to, concurrently with, and/or following step (a) or step (b), with at least a first media comprising spectinomycin to select transformed cells comprising said selectable marker, the method further comprises transforming at least a first cell of the explant with a heterologous nucleic acid is carried out by bacterially-mediated transformation or microprojectile bombardment.

In some embodiments, the explant is further defined as having been excised from a seed comprising 3% to 25% internal moisture content, or a hydrated or germinating seed comprising 26% to 80% internal moisture content, or comprises a tissue of the group consisting of: meristem, immature embryo, embryo, embryonic axis, cotyledon, hypocotyl, mesocotyl, leaf, primary leaf base, leaf disc, shoot tip, and plumule. In certain embodiments, the explant is further defined as having been excised from a germinated or imbibed seed. In other embodiments, the explant is not contacted with a media comprising spectinomycin subsequent to step (a). In particular embodiments, the first media is a liquid. In other embodiments, one or more of steps (a)-(b) are automated.

In another aspect, the invention provides a nucleic acid construct comprising two sequences conferring resistance to spectinomycin or streptomycin, wherein the first sequence is operably linked to a promoter active in a plant cell, and the second sequence is operably linked to a promoter active in a prokaryotic cell. In a particular embodiment, the sequences conferring resistance to spectinomycin or streptomycin encode a polypeptide comprising aminoglycoside-3'-adenyl-transferase (aadA) activity. In a more particular embodiment, at least one of the sequences comprises SEQ ID NO:1 or SEQ ID NO:2.

BRIEF DESCRIPTION OF THE DRAWINGS

The following drawings are part of the present specification and are included to further demonstrate certain aspects of the present invention. The invention may be better understood by reference to the drawing in combination with the detailed description of specific embodiments presented herein.

DETAILED DESCRIPTION OF THE INVENTION

Figure 1:
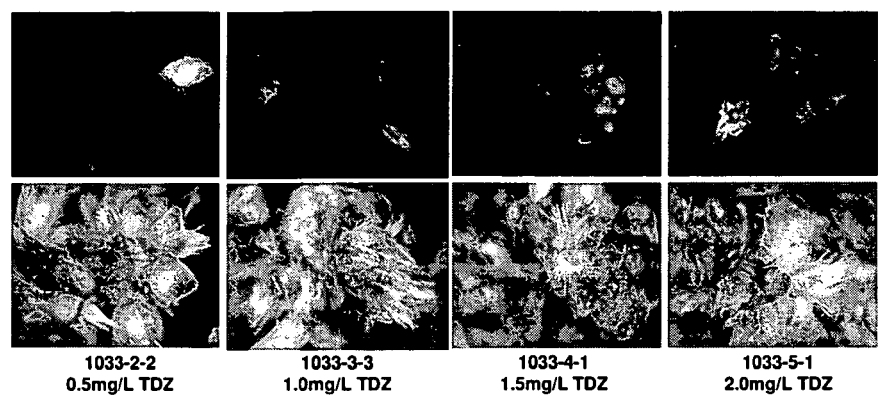
FIG. 1: Magnified details of four soy explants from treatments with different levels of TDZ added to the inoculum/co-cultivation medium. Each explant developed de novo buds/shoots (bottom) and some were GFP-positive (top). The pictures on the top row were taken in a microscope with a modified blue light source that detects GFP-expressing tissue by fluorescence. The same images were taken with a standard white light source to show all the developed buds/shoots (bottom row).

The following is a detailed description of the invention provided to aid those skilled in the art in practicing the present invention. Those of ordinary skill in the art may make modifications and variations in the embodiments described herein without departing from the spirit or scope of the present invention.

The invention provides methods and compositions for use of spectinomycin as a selective agent for preparing, screening, transforming, and regenerating explants from soybean, corn, cotton, or canola plants, among others, to obtain transformed plant tissues and plants. In some aspects, various portions of the described methods may be automated, high-throughput procedures. An explant such as a mature or immature embryo is obtained, for instance from a seed, and may be transformed, for instance via a bacterially-mediated or microprojectile bombardment approach. In certain embodiments, at the time that a heterologous DNA is contacting the explant, or subsequently, the explant is contacted by a cytokinin selected from the group consisting of thidiazuron, BAP (6-Benzylaminopurine), kinetin, CPPU (N-(2-Chloro-4-pyridyl)-N'-phenylurea), 2iP (6-(y,y-Dimethylallylamino) purine), Zeatin, Zeatin-riboside, Adenine, and TIBA (2,3,5-Triiodobenzoic acid)) or other agent like dikegulac. To facilitate the contacting of an explant with the cytokinin, the cytokinin may be added to the bacterial inoculum to be used in the transformation prior to the contacting of the explant with the inoculum. In certain embodiments, the cytokinin which is employed is BAP at a concentration of about 0-3 mg/L or about 0.25-3 mg/L, or TDZ (at about 0-3 mg/l or about 0.25-3 mg/L). In certain embodiments, the cytokinin or other agents may also be added during seed imbibition to treat the explants before they are excised.

Use of spectinomycin, with or without cytokinin treatment, at concentrations of between 15-1500 mg/L is contemplated, for instance about 25, 50, 100, 150, 250, 300, 500, 1000, or 1500 mg/L. If a method for bacterially-mediated transformation is used, the spectinomycin may be added to the bacterial inoculum prior to its contacting the explant. Alternatively, if a bacterially-mediated or microprojectile-mediated transformation method is used, the spectinomycin may be added prior to, concurrently, or following the step of transforming a soybean, corn, cotton, or canola cell, so as to select for cells transformed with a heterologous nucleic acid. Spectinomycin may also be employed as a "pulse" for a portion of the period of time for a described tissue culture growth step, such as the pre-culture step, co-cultivation step, delay step, or selection step, and optionally at a higher concentration of about 1000 mg/L.

The transformation frequencies ("TFs") obtained using the methods and compositions described herein have not been achievable in the prior art. Thus, an increase in TF of 2-10 or 5-10 fold (and even higher in some cases) over that found, for instance, when using glyphosate or dicamba as the selective agent for transformation of soybean or cotton, has been achieved. Additionally, the increased transformation efficiency allows for development of an efficient 2 T-DNA transformation system using spectinomycin selection, thus allowing for stacking of transgenic traits by transformation and crossing of plants already comprising a transgenic trait with a nucleic acid encoding an additional trait of interest, and then screening for plants also comprising the nucleic acid encoding the additional trait.

Combined with an increased TF, the methods described also allow for more rapid regeneration of candidate transformed plant tissues, increased efficiency in identifying and growing transformed shoots and plants, and reduced costs and ergonomic burden, while simplifying and reducing the labor necessary to produce transformed plants. For instance, after spectinomycin resistant shoots with green (i.e. spectinomycin resistant) buds or leaves have elongated and are screenable or scoreable as being spectinomycin resistant, they may be placed in soil or on a soil substitute such as on a rooting medium, in the presence or absence of the selective agent. Shoots elongating from such an explant are routinely shown to be transgenic and give rise to $R_1$ and subsequent progeny that are transgenic, while the roots developing from such explants may be transgenic or non-transgenic. Thus, a plant comprising a transgenic shoot and a partly or fully non-transgenic root system is also contemplated. A method for regenerating a whole plant from transgenic shoots from transformed meristematic tissue while roots are non-transgenic, by culturing of transformed tissue on a medium lacking a selective agent, is also contemplated. The described methods thus allow for a significant decrease in the time spent under selective conditions and in usage of the selective agent, thus reducing potential costs as well.

In order to provide a clear and consistent understanding of the specification and the claims, including the scope given to such terms, the following definitions are provided.

"Embryo" is part of a seed, consisting of precursor tissues (meristematic tissues) for the leaves, stem, and root. Once the embryo begins to grow (germinate), it becomes a seedling plant.

"Meristem" or "meristematic tissue" consists of undifferentiated cells, the meristematic cells, which differentiate to produce multiple plant structures including stem, roots, leaves, germline tissue and seeds. The meristematic cells are the targets for transformation to obtain transgenic plants.

"Explant" is a term used to refer to target material for transformation, comprising meristematic tissue. It may refer to plant tissues including, without limitation, one or more embryos, cotyledons, hypocotyls, leaf bases, mesocotyls, plumules, protoplasts, and embryonic axes.

"Chimeric plants" are plants that are composed of tissues that are not genetically identical, i.e., the plants will have only a portion or fraction of their tissues transformed, whereas the remainder of the tissues are not genetically transformed.

"Germline transformation" occurs when the gene of interest is transformed into cells that give rise to pollen or ovule thus into seeds.

The explants may be transformed by a selected heterologous DNA sequence, and transgenic plants may be regenerated therefrom, without the need for generating a callus cell culture from the transformed explant in order to obtain transgenic progeny plants. The selected heterologous DNA sequence may for instance encode a screenable or selectable marker, and/or comprise a gene of agronomic interest specifying a trait to be exhibited by a soybean, corn, cotton, or canola plant or cell resulting from the expression of the heterologous nucleic acid. The trait may be agronomically useful, for instance resulting in enhanced yield, herbicide tolerance, pest or pathogen resistance, or environmental adaptability, among other phenotypes. The trait may also specify production of a desired end-product.

Such transformation and regeneration methods allow for a fast and efficient high-throughput process for generating transformed plants. Mechanization significantly reduces the estimated man-hours needed to produce 10,000 explants, for instance in the case of cotton from about 40 to only 2.4 hours, significantly saving labor costs. Such a technique allows larger numbers of transgenes to be tested and higher quality events to be chosen for further analysis, as only a very small number of transformation events are expected to exhibit the most desired expression profiles suitable for commercial development. A mechanized excision process also allows better timing and scheduling of transformation steps, because of increased flexibility in explant delivery. Use of a mechanized process for explant excision may provide significant monetary, safety and flexibility benefits. However, explant preparation may also be performed manually.

Prior to imbibition, germination, and/or explant excision, seeds may be subjected to a sterilization step as well as a culling step, to avoid microbial contamination, to remove seeds with a high degree of bacterial or fungal contamination, and also to remove seeds that may for any reason be unlikely to produce viable explant tissue for use with the present invention. Culling may be carried out, for example, based on parameters such as the size, color, or density of the seed or other characteristics, including chemical composition characteristics. Examples of culling methods may include the use of an automatic scale after size sorting. An optical sorter suitable for this purpose is the Sortex 3000 Series Color Sorter (Buhler-Sortex KK, Yokohama, Japan). Other culling techniques may also be employed including culling by moisture content. After excision, explants may also be subjected to a rehydration or pre-culture step prior to being transformed with a heterologous nucleic acid.

In specific embodiments, excision is mechanically performed using rollers that crush seeds applied to their faces, which can be counter-rotating. The gap between the rollers may be adjusted based on the size of the applied seeds. Roller material may, for instance, be elastomeric or metallic. In certain embodiments, stainless steel rollers have been found to retain beneficial working qualities even following repeated and sustained use. For use with cotton seeds, rollers with secondary grooves have been found to efficiently grip and crush seed with minimal damage to the meristematic explant seed fraction. Methods for mechanized excision of plant explants are known, for instance see U.S. Provisional Patent Application Ser. Nos. 60/894,096 and 60/915,066, and U.S. Patent Application Publication No. US2005/0005321, incorporated by reference herein in their entirety.

In one embodiment, an explant prepared in accordance with the invention may be defined as having an internal moisture of about 4-25%, including about 4, 5, 6, 7, 8, 9, 10, 11, 12, 13, 14, 16, 17, 18, 19, 20, 21, 22, 23, 24, and 25% internal moisture, and specifically including all ranges derivable between any two such values. In particular embodiments, seeds from which explants are to be prepared may be harvested at a predetermined internal moisture suitable for isolating transformable material therefrom. In certain non-limiting embodiments, seeds from which explants are obtained may be defined as having an internal moisture of about 3-25%, including about 3, 4, 5, 6, 7, 8, 9, 10, 11, 12, 13, 14, 16, 17, 18, 19, 20, 21, 22, 23, 24, and 25% internal moisture, and specifically including all ranges derivable between any two such values, such as, for example, from about 4% to 16%. In certain embodiments, brittleness of seeds may be altered by manipulating moisture content, allowing for efficient splitting of seeds and preparation of explants. For instance, an internal moisture content such as 3% to 7% may be advantageous. Seeds may be held at such moisture contents or any other moisture content yielding stable storage conditions (and transformable explants) prior to use. The seeds in certain embodiments may be soybean, corn, cotton, or canola seeds.

Dry explants (explants that have been excised from seed under low moisture conditions) or dried wet explants (explants that have been excised from seed following hydration/imbibition and are subsequently dehydrated and stored) of various ages may be used. In one embodiment, explants are relatively "young" in that they have been removed from seeds for less than a day, for example, from about 1 to 24 hours, such as about 2, 3, 5, 7, 10, 12, 15, 20, or 23 hours prior to use. In other embodiments, explants may be stored for longer periods, including days, weeks, months or even years, depending upon storage conditions used to maintain explant viability. Those of skill in the art in particular will understand that storage times may be optimized such that the quality and/or yield of transformants as well as the efficiency of the transformation process is maximized. This can be carried out for any particular transformation protocol, for example, such as *Agrobacterium*-mediated transformation, microprojectile bombardment transformation, as well as other transformation procedures.

In some embodiments, a dry seed or an explant may be first primed, for example, by imbibition of a liquid such as water or a sterilization liquid, redried, and later used for transformation and regeneration. In other embodiments, the seed or the explant may be primed by raising the internal seed moisture content to greater than 30%, holding the seed or the explant at a time point, and then re-initiating imbibition at a later time point. In an alternative embodiment, the seed or the explant may be primed by raising the internal moisture content to greater than 30%, storing the seed or the explant for a predetermined period, drying the seed or the explant to the internal moisture content of below 20%, and then re-initiating imbibition.

Regenerable transformable explants may be harvested that contain no, some, or a part of each cotyledon remaining attached to the embryonic tissue, for example as much as ¼ of the cotyledon. These explants are considered substantially similar, as they may each result in a stable transformed plant. The explant should however contain at least some of the meristematic region of the embryo such that typically the explant can produce a shoot within 12 weeks of the onset of tissue culture growth conditions.

The explant may be recovered from a hydrated seed, from dry storable seed, from a partial rehydration of dried hydrated explant, wherein "hydration" and "rehydration" is defined as a measurable change in internal seed moisture percentage, or from a seed that is "primed"; that is, a seed that has initiated germination but has been appropriately placed in stasis pending favorable conditions to complete the germination process. Those of skill in the art will be able to use various hydration methods and optimize length of incubation time prior to transformation. The resulting novel explant is storable and can germinate and or be transformed when appropriate conditions are provided. Thus the new dry, storable meristem explant may be referred to as an artificial seed.

Following excision, one of skill in the art may store the explant according to the disclosed methods prior to subsequent use. Methods and parameters for drying, storing, and germinating seed are known in the art (e.g. Senaratna et al., 1983; Vertucci and Roos, 1990; Chai et al., 1998). Storage of excised meristems in accordance with the current invention may be carried out using modifications of such storage conditions as desired. Any such conditions may be used as desired, including at temperatures, for example, of from about −80° C. to about 60° C. Temperatures of about −20° C. to room temperature in particular have been found to function well, but the invention is in no way limited to these temperatures.

The data described in the Examples illustrates, for instance, that stored seed explants comprising meristematic tissue may remain viable and useful for subsequent genetic transformation and regeneration for weeks or months following excision from seeds (e.g. Example 12). Manipulation of excision, sterilization, storage, hydration, redehydration, and transformation parameters allows development of efficient automated high throughput plant transformation protocols. Rehydration, priming and hydration conditions are also presented. A typical protocol for machine excision, may involve placing seeds for 15 minutes in a bleach solution of 200 ppm active Cl, followed by a 2 hour period of no liquid exposure, followed by an overnight hydration in either bean germination medium (BGM) or a bleach solution of 50 ppm active Cl.

A number of parameters for obtaining and handling explants may be varied. In one embodiment, the excision method may be manual; in an alternative embodiment excision occurs by an automated process. In other embodiments sterilization may be performed by contacting a seed or explant with a liquid sterilizing agent. The addition to a co-culture media (like INO) of nystatin (50 ppm) and thiabendazole (10 ppm) dissolved in DMSO (1.0 ml of DMSO per liter of INO) may improve the health of explants, likely by controlling yeasts and fungi commonly found in and on seeds and can be a useful tool when performing large and/or automated tissue culture. In an alternative embodiment, a seed or an explant may be contacted with a gaseous sterilizing agent. In an alternative embodiment, a seed or an explant may be contacted with an irradiating sterilizing agent such as UV light. In an alternative embodiment, a seed or an explant may be sterilized by subjecting the seed or the explant to a brief period of high temperatures so as to reduce the vigor of biological contaminants such as adventitious bacteria and fungi on the surface of the seed or the explant without reducing the vigor of the seed or the explant. This can be achieved at a temperature higher than 40° C.; preferably the temperature is between 40° C. to 90° C. The temperature can be raised, for instance, by either forced heated air or steam. Such temperatures can be provided by dryers produced by Bry-Air Inc. (Sunbury, Ohio, USA). In still a further embodiment, moisture content of the seed at the time of excision may be varied. In another embodiment, the temperature of the seed at the time of excision may be varied. In other embodiments, a storage parameter following excision may be varied. For instance, in one embodiment the relative humidity under which explant storage occurs may be varied. In another embodiment, the explant storage temperature may be varied. In yet other embodiments, the length of explant storage time may vary. In yet other embodiments, the composition of the medium in which the explant is stored may vary. Further parameters that may be manipulated include hydration and rehydration media compositions, incubation temperature, length of time, and transformation methods, among others.

Following excision, the invention also provides methods and apparati for screening to transformable meristematic explant material from non-transformable damaged explants, cotyledons, seed coats, and other debris. The methods may be performed manually, or may be partially or fully mechanized. In certain embodiments, the screening process is substantially mechanized. For instance, one or more steps of sieving may be performed, using sieves of appropriate size based on size of the seeds being crushed and the explants being isolated. Bulk yield of crushed seed that has passed through the rollers may be put through a series of separation sieves, such that unwanted large and small debris are separated from the desired explant by size exclusion. This may be effectively accomplished, for instance with cottonseed material, using U.S. Standard sieves such as: #8 (2.36 mm opening), #10 (2.0 mm opening), #16 (1.18 mm opening), and others as appropriate (e.g. elongated window sieves such as ¹⁄₁₆"×¾", ¹⁄₁₈"×¾", ¹⁄₁₉"×½", or ¹⁄₂₀"×½"). Sieves with other opening sizes may be fabricated as needed for given seed sizes, based on the size of material being applied.

The length of time for the screening process and the vigor of sieving may also be adjusted to enhance the throughput and/or yield of the process.

Other screening methods may also be utilized, such as by measuring differential buoyancy in solutions of explant material versus debris. A fraction of material that floats in an aqueous solution has been found to be enriched for intact transformable explants. A dry-excised explant may be utilized. Combinations of such screening methods may also be used. The fraction of material with transformable explants may comprise both meristematic tissues and other tissues, such as portions of cotyledons. The explant should however contain at least some of the meristematic region such that typically the explant can produce a bud or shoot within 12 weeks of the onset of appropriate growth conditions.

In certain embodiments the excised and screened tissues may be transformed with a heterologous gene of interest. Various methods have been developed for transferring genes into plant tissue including high velocity microprojection, microinjection, electroporation, direct DNA uptake and, bacterially-mediated transformation. Bacteria known to mediate plant cell transformation include a number of species of the Rhizobiaceae, including, but not limited to, *Agrobacterium* sp., *Sinorhizobium* sp., *Mesorhizobium* sp., and *Bradyrhizobium* sp. (e.g. Broothaerts et al., 2005; U.S. Patent Application Publication 2007/0271627). Targets for such transformation have often been undifferentiated callus tissues, although differentiated tissue also has been used for transient and stable plant transformation, and may be in this instance. Co-culture and subsequent steps may be performed in dark conditions, or in the light, e.g. lighted Percival incubators, for instance for 2 to 5 days (e.g. a photoperiod of 16 hours of light/8 hours of dark, with light intensity of ≥5 µE, such as about 5-200 µE or other lighting conditions that allow for normal plastid development) at a temperature of approximately 23 to 25° C., and may be performed at up to about 35° C. or 40° C.

In designing a vector for the transformation process, one or more genetic components are selected that are introduced into the plant cell or tissue. Genetic components can include any nucleic acid that is introduced into a plant cell or tissue using the method according to the invention. In one embodiment, the genetic components are incorporated into a DNA composition such as a recombinant, double-stranded plasmid or vector molecule comprising at least one or more of following types of genetic components: (a) a promoter that functions in plant cells to cause the production of an RNA sequence, (b) a structural DNA sequence that causes the production of an RNA sequence that encodes a product of agronomic utility, and (c) a 3' non-translated DNA sequence that functions in plant cells to cause the addition of polyadenylated nucleotides to the 3' end of the RNA sequence.

The vector may contain a number of genetic components to facilitate transformation of the plant cell or tissue and regulate expression of the structural nucleic acid sequence. In one preferred embodiment, the genetic components are oriented so as to express an mRNA, that in an optional embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase enzyme and subsequent processing of the mRNA primary transcript inside the nucleus. This processing involves a 3' non-translated region that adds polyadenylated nucleotides to the 3' ends of the mRNA. Means for preparing plasmids or vectors containing the desired genetic components are well known in the art.

When a DNA construct contains more than one T-DNA, these T-DNAs and the transgenes contained within may be integrated into the plant genome at separate loci. This is referred to as "co-transformation" (U.S. Pat. No. 5,731,179, WO 00/18939). The process of co-transformation, where two T-DNAs are at different loci in the plant genome and therefore segregate independently in the progeny, can be achieved by delivery of the T-DNAs with a mixture of Agrobacteria transformed with plasmids carrying the separate T-DNA. Co-transformation can also be achieved by transforming one *Agrobacterium* strain with two binary DNA constructs, each containing one T-DNA (e.g. Daley et al., 1998). Two T-DNAs may also be designed on a single DNA vector, followed by transforming the vector into a plant cell and then identifying the transgenic cells or plants that have integrated the T-DNAs at different loci (U.S. Pat. No. 5,731,179, WO 00/18939, Komari et al, 1996; U.S. Pat. No. 7,288,694).

A two T-DNA system is a useful method to segregate the marker gene from the agronomically important gene of interest (GOI) in a transgenic plant. The marker gene generally has no further utility after it has been used to select or score for the transformed plant cell. A single DNA vector carrying the two-T-DNAs is one method to construct a two T-DNA transformation system. However because of the occurrence of both T-DNAs on a single DNA construct, both may be transferred into the plant genome at the same locus. This occurs when one of the border DNA molecule of the first T-DNA is not recognized during the integration process. This reduced efficiency adds to the cost of producing the events and selecting for the individuals that have T-DNAs integrated at an independent locus. It thus also may be desirable to have DNA constructs and a method wherein it is possible to chemically select against individuals that have incorporated the two T-DNAs at the same locus, while screening for the presence/absence and linkage status of each of the T-DNAs.

Transcription of DNA into mRNA is regulated by a region of DNA usually referred to as the "promoter". The promoter region contains a sequence of bases that signals RNA polymerase to associate with the DNA and to initiate the transcription into mRNA using one of the DNA strands as a template to make a corresponding complementary strand of RNA. A number of promoters that are active in plant cells have been described in the literature. Such promoters would include but are not limited to the nopaline synthase (NOS) and octopine synthase (OCS) promoters that are carried on Ti plasmids of *Agrobacterium tumefaciens*, the caulimovirus promoters such as the cauliflower mosaic virus (CaMV) 19S and 35S promoters and the Figwort mosaic virus (FMV) 35S promoter, and the enhanced CaMV35S promoter (e35S). A variety of other plant gene promoters that are regulated in response to environmental, hormonal, chemical, and/or developmental signals, also can be used for expression of heterologous genes in plant cells, including, for instance, promoters regulated by (1) heat (Callis et al., 1988, (2) light (e.g., pea RbcS-3A promoter, Kuhlemeier et al., (1989); maize RbcS promoter, Schaffner et al., (1991); (3) hormones, such as abscisic acid (Marcotte et al., 1989, (4) wounding (e.g., Wuni, Siebertz et al., 1989); or other signals or chemicals. Tissue specific expression is also known. As described below, it is preferred that the particular promoter selected should be capable of causing sufficient expression to result in the production of an effective amount of the gene product of interest. Examples describing such promoters include without limitation U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that may find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987; U.S. Pat. Nos. 6,051,753; 5,378,619), the sucrose synthase promoter (Yang et al., 1990), the R gene complex promoter (Chandler et al., 1989), and the chlorophyll a/b binding protein gene promoter, PC1SV (U.S. Pat. No. 5,850,019), and AGRtu.nos (GenBank Accession V00087; Depicker et al, 1982; Bevan et al., 1983) promoters.

Promoter hybrids can also be constructed to enhance transcriptional activity (U.S. Pat. No. 5,106,739), or to combine desired transcriptional activity, inducibility and tissue specificity or developmental specificity. Promoters that function in plants include but are not limited to promoters that are inducible, viral, synthetic, constitutive as described, and temporally regulated, spatially regulated, and spatio-temporally regulated. Other promoters that are tissue-enhanced, tissue-specific, or developmentally regulated are also known in the art and envisioned to have utility in the practice of this invention.

The promoters used in the DNA constructs (i.e. chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression.

The mRNA produced by a DNA construct of the present invention may also contain a 5' non-translated leader sequence. This sequence can be derived from the promoter selected to express the gene and can be specifically modified so as to increase or decrease translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes (see, for example U.S. Pat. No. 5,362,865). Examples of non-translation leader sequences include maize and *petunia* heat shock protein leaders (U.S. Pat. No. 5,362,865), plant virus coat protein leaders, plant rubisco leaders, GmHsp (U.S. Pat. No. 5,659,122), PhDnaK (U.S. Pat. No. 5,362, 865), AtAnt1, TEV (Carrington and Freed, 1990), and AGRtu.nos (GenBank Accession V00087; Bevan et al., 1983). Other genetic components that serve to enhance expression or affect transcription or translational of a gene are also envisioned as genetic components.

The 3' non-translated region of the chimeric constructs may contain a transcriptional terminator, or an element having equivalent function, and a polyadenylation signal that functions in plants to cause the addition of polyadenylated nucleotides to the 3' end of the RNA. The DNA sequences are referred to herein as transcription-termination regions. The regions are required for efficient polyadenylation of transcribed messenger RNA (mRNA). RNA polymerase transcribes a coding DNA sequence through a site where polyadenylation occurs. Examples of suitable 3' regions are (1) the 3' transcribed, non-translated regions containing the polyadenylation signal of *Agrobacterium* tumor-inducing (Ti) plasmid genes, such as the nopaline synthase (NOS; Fraley et al., 1983) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea (European Patent Application 0385 962).

In one embodiment, the vector contains a selectable, screenable, or scoreable marker gene. These genetic components are also referred to herein as functional genetic components, as they produce a product that serves a function in the identification of a transformed plant, or a product of agronomic utility. The DNA that serves as a selection or screening device may function in a regenerable plant tissue to produce a compound that would confer upon the plant tissue resistance to an otherwise toxic compound. A number of screenable or selectable marker genes are known in the art and can be used in the present invention. Genes of interest for use as a marker would include but are not limited to GUS, green fluorescent protein (GFP), luciferase (LUX), among others. In certain embodiments, the vector comprises an aadA gene with associated regulatory elements encoding resistance to spectinomycin in plant cells. In a particular embodiment, the aadA gene comprises a chloroplast transit peptide (CTP) sequence that directs the transport of the AadA gene product to the chloroplast of a transformed plant cell. In other embodiments, the vector comprises a spectinomycin resistance gene with appropriate regulatory elements designed for expression in a bacterial cell, such as an *Agrobacterium* cell, so that the selection reagent may be added to a co-cultivation medium, and allowing obtention of transgenic plants for instance without further use of the selective agent after the co-culture period.

The present invention can be used with any suitable plant transformation plasmid or vector containing a selectable or screenable marker and associated regulatory elements as described, along with one or more nucleic acids expressed in a manner sufficient to confer a particular desirable trait. Examples of suitable structural genes of agronomic interest envisioned by the present invention would include but are not limited to genes for disease, insect, or pest tolerance, herbicide tolerance, genes for quality improvements such as yield, nutritional enhancements, environmental or stress tolerances, or any desirable changes in plant physiology, growth, development, morphology or plant product(s) including starch production (U.S. Pat. Nos. 6,538,181; 6,538,179; 6,538,178; 5,750,876; 6,476,295), modified oils production (U.S. Pat. Nos. 6,444,876; 6,426,447; 6,380, 462), high oil production (U.S. Pat. Nos. 6,495,739; 5,608, 149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,541,259; 5,985,605; 6,171,640), biopolymers (U.S. Pat. RE37,543; 6,228,623; 5,958,745 and U.S. Patent Publication No. US20030028917). Also environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700). Any of these or other genetic elements, methods, and transgenes may be used with the invention as will be appreciated by those of skill in the art in view of the instant disclosure.

Alternatively, the DNA sequences of interest can affect these phenotypes by encoding a an RNA molecule that causes the targeted inhibition of expression of an endogenous gene via gene silencing technologies such as antisense-, co-suppression-mediated mechanisms, RNAi technologies including miRNA (e.g., U.S. Patent Application Publication 2006/0200878).

Exemplary nucleic acids that may be introduced by the methods encompassed by the present invention include, for example, DNA sequences or genes from another species, or even genes or sequences that originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes that are normally present yet that one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In one embodiment, transformation of plant tissue is performed by a bacterially-mediated method, such as an Agrobacterium or other Rhizobia-mediated method, and the DNA sequences of interest are present on one or more T-DNAs (U.S. Pat. Nos. 6,265,638, 5,731,179; U.S. Patent Application Publications US2005/0183170; 2003110532) or other sequence (e.g., vector backbone) that is transferred into a plant cell. The T-DNAs may be bound by RB and/or LB sequences or may have no border sequences. The sequences that may be transferred into a plant cell may be present on one transformation vector in a bacterial strain being utilized for transformation. In another embodiment, the sequences may be present on separate transformation vectors in the bacterial strain. In yet another embodiment, the sequences may be found in separate bacterial cells or strains used together for transformation.

The DNA constructs used for transformation in the methods of present invention may also contain the plasmid backbone DNA segments that provide replication function and antibiotic selection in bacterial cells, for example, an Escherichia coli origin of replication such as ori322, a broad host range origin of replication such as oriV or oriRi, and a coding region for a selectable marker such as Spec/Strp that encodes for aminoglycoside adenyltransferase (aadA) conferring resistance to spectinomycin or streptomycin (e.g. U.S. Pat. No. 5,217,902; or Sandvang, 1999). For plant transformation, the host bacterial strain is often Agrobacterium tumefaciens ABI, C58, LBA4404, EHA101, or EHA105 carrying a plasmid having a transfer function for the expression unit. Other strains known to those skilled in the art of plant transformation can function in the present invention.

Bacterially-mediated gene delivery (e.g. Agrobacterium-mediated; U.S. Pat. Nos. 5,563,055; 5,591,616; 5,693,512; 5,824,877; 5,981,840) can be made into cells in the living meristem of an embryo excised from a seed (e.g. U.S. Pat. No. 6,384,301), and the meristematic region may be cultured in the presence of a selection agent such as spectinomycin. The result of this step is the termination or at least growth retardation of most of the cells into which the foreign genetic construction has not been delivered with the simultaneous formation of shoots, which arise from a single transformed meristematic cell, or small cluster of cells including transformed meristematic cells. In particular embodiments, the meristem can be cultivated in the presence of spectinomycin, streptomycin or other selective agent, tolerance to which is encoded by the aadA gene. Examples of various selectable markers and genes providing resistance against them are disclosed in Miki and McHugh, 2004.

In light of this disclosure, numerous other possible regulatory elements, and other sequences of interest will be apparent to those of skill in the art. Therefore, the foregoing discussion is intended to be exemplary rather than exhaustive.

Screenable or scorable markers can be employed to identify transgenic sectors/and or plants. Exemplary markers are known and include β-glucuronidase (GUS) that encodes an enzyme for various chromogenic substrates (Jefferson et al., 1987a; Jefferson et al., 1987b); an R-locus gene, that encodes a product that regulates the production of anthocyanin pigments (red color) in plant tissues (Dellaporta et al., 1988); a β-lactamase gene (Sutcliffe et al., 1978); a gene that encodes an enzyme for that various chromogenic substrates are known (e.g., PADAC, a chromogenic cephalosporin); a luciferase gene (Ow et al., 1986); a xylE gene (Zukowsky et al., 1983) that encodes a catechol dioxygenase that can convert chromogenic catechols; an α-amylase gene (Ikatu et al., 1990); a tyrosinase gene (Katz et al., 1983) that encodes an enzyme capable of oxidizing tyrosine to DOPA and dopaquinone that in turn condenses to melanin; green fluorescence protein (Elliot et al., 1999) and an α-galactosidase. As is well known in the art, other methods for plant transformation may be utilized, for instance as described by Miki et al., (1993), including use of microprojectile bombardment (e.g. U.S. Pat. No. 5,914,451; McCabe et al., 1991; U.S. Pat. Nos. 5,015,580; 5,550,318; 5,538,880).

A variety of tissue culture media are known that, when supplemented appropriately, support plant tissue growth and development, including formation of mature plants from excised meristems. These tissue culture media can either be purchased as a commercial preparation or custom prepared and modified by those of skill in the art. Examples of such media include, but are not limited to those described by Murashige and Skoog, (1962); Chu et al., (1975); Linsmaier and Skoog, (1965); Uchimiya and Murashige, (1962); Gamborg et al., (1968); Duncan et al., (1985); McCown and Lloyd, (1981); Nitsch and Nitsch (1969); and Schenk and Hildebrandt, (1972), or derivations of these media supplemented accordingly. Those of skill in the art are aware that media and media supplements such as nutrients and growth regulators for use in transformation and regeneration are usually optimized for the particular target crop or variety of interest. Tissue culture media may be supplemented with carbohydrates such as, but not limited to, glucose, sucrose, maltose, mannose, fructose, lactose, galactose, and/or dextrose, or ratios of carbohydrates. Reagents are commercially available and can be purchased from a number of suppliers (see, for example Sigma Chemical Co., St. Louis, Mo.; and PhytoTechnology Laboratories, Shawnee Mission, Kans.).

Transgenic plants may be regenerated from a transformed plant cell by methods and compositions disclosed here, such as, but not limited to, spectinomycin Protocols "A" through "D", as performed on soybean, corn, cotton, or canola explants. A transgenic plant formed using *Agrobacterium* transformation methods typically (although not always) contains a single simple recombinant DNA sequence inserted into one chromosome and is referred to as a transgenic event. Such transgenic plants can be referred to as being heterozygous for the inserted exogenous sequence. A transgenic plant homozygous with respect to a transgene can be obtained by sexually mating (selfing) an independent segregant transgenic plant that contains a single exogenous gene sequence to itself, for example an $R_0$ plant, to produce R1 seed. One fourth of the $R_1$ seed produced will be homozygous with respect to the transgene. Germinating $R_1$ seed results in plants that can be tested for zygosity, typically using a SNP assay or a thermal amplification assay that allows for the distinction between heterozygotes and homozygotes (i.e., a zygosity assay).

To confirm the presence of the exogenous DNA or "transgene(s)" in the transgenic plants a variety of assays may be performed. Such assays include, for example, "molecular biological" assays, such as Southern and northern blotting and PCR™, INVADER assays; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Once a transgene has been introduced into a plant, that gene can be introduced into any plant sexually compatible with the first plant by crossing, without the need for ever directly transforming the second plant. Therefore, as used herein the term "progeny" denotes the offspring of any generation of a parent plant prepared in accordance with the instant invention, wherein the progeny comprises a selected DNA construct. A "transgenic plant" may thus be of any generation. "Crossing" a plant to provide a plant line having one or more added transgenes or alleles relative to a starting plant line is defined as the techniques that result in a particular sequence being introduced into a plant line by crossing a starting line with a donor plant line that comprises a transgene or allele. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

The present invention also provides for plant parts or a plant produced by the methods of the present invention. Plant parts, without limitation, include fruit, seed, endosperm, ovule, pollen, leaf, stem, and roots. In a preferred embodiment of the present invention, the plant part is a seed.

In another aspect, the invention provides an isolated nucleic acid molecule comprising a sequence that encodes a polypeptide comprising a chloroplast transit peptide (CTP)-aadA translational fusion. In certain embodiments, the nucleic acid comprises SEQ ID NO:2.

EXAMPLES

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Preparation of Explant and Inoculation Material

A. Soybean

In order to obtain meristematic explant material, soybean seeds (e.g. cv. A3525; Asgrow Seed Company; were processed to separate the embryo, comprising meristematic tissues, from other tissues including the seed coat and cotyledon(s). Manual preparation of explants provides tissue which is suitable for *Agrobacterium*-mediated transformation of soybean meristems (U.S. Pat. No. 6,384,301), and Particle mediated transformation methods (U.S. Pat. No. 5,914,451) are known. Mechanical methods of extracting explants have also been described in U.S. Patent Application Publication 20050005321 and U.S. Patent Application Publication 20060059589. All of these methods result in a meristem explant that is sufficiently transformable by the described methods.

B. Cotton

Cotton seeds were mechanically processed to excise and isolate their meristematic tissues. Alternatively, cotton explants may be prepared by excision of the embryonic axis from the seed, cotyledons, and hypocotyl (e.g. McCabe and Martinell, 1993). In order to obtain transformable meristematic explant material, cotton seeds (e.g. from genotypes STN474 (Stoneville Pedigreed Seed Co., Stoneville, Miss.), Delta Pearl (Delta and Pine Land Co., Scott, Miss.), DP5415, DP393, 00S04 (Delta and Pine Land Co.), Sure-Grow501 or SureGrow747 (Sure Grow Cotton Seed Company, Maricopa, Ariz.) were processed as follows to separate the embryo, comprising meristematic tissues, from the seed coat and cotyledon(s). Cotton seeds were removed from storage at 4° C. or −20° C. and brought to room temperature. Seeds were weighed out, placed into a sterile germinator unit, and surface-sterilized in 50% Clorox (sodium hypochlorite) for 5 min. Seeds were then rinsed 3 times with sterile distilled water and were hydrated in a liquid hydration medium (CSM) at 28° C. in the dark for about 18 hrs (range of 14 to 42 hours). Alternatively, the germination temperature may be lower, for instance about 23° C. The CSM medium contained 200 mg/L carbenicillin (PhyoTechnology Laboratories, Shawnee Mission, Kans.), 125 mg/L cefotaxime (Midwest Scientific, St. Louis, Mo.), 30 mg/L BRAVO 75 (Carlin, Milwaukee, Wis.) and 30 mg/L Captan 50 (Carlin). Other solutions have also successfully been used to hydrate the cotton seeds, including sterile deionized water or water containing a weak concentration of bleach typically 50 to 1000 ppm sodium hypochlorite. Following hydration, seeds may be used immediately, or stored at refrigeration temperatures for up to a week prior to further processing. Mechanical excision of cotton explants may also be utilized (WO92/15675; Keller et al., 1997; McCabe & Martinell, 1993; U.S. Patent Publication 2005/0005321).

C. Preparation of *Agrobacterium* for Inoculation and Co-Cultivation

*Agrobacterium* strain C58 containing a binary vector with one or two plant expression cassettes as described above was inoculated, from a glycerol stock, into a liquid LB medium (10 g/L sodium chloride, 5 g/L yeast extract, 10 g/L bactotryptone) containing 75 mg/mL spectinomycin and 50 mg/mL kanamycin. The liquid culture was allowed to grow at 28° C. at 200 rpm on a rotary shaker overnight. After the optical density ($OD_{660}$) of the overnight culture reached the target range of 0.4-1.2, the bacterial culture was centrifuged at 3500 rpm for approximately 20-25 min to pellet the cells.

Following removal of the supernatant, the pellet was re-suspended in 10 mL of an inoculation medium (INO, Table 1). The $OD_{660}$ (an indirect measurement of bacterial concentration) was measured and diluted and adjusted to $OD_{660}$ about 0.28-0.32. Once prepared *Agrobacterium* cultures are prepared, plant explants are exposed to the inoculum, briefly exposed to sonication energy from a standard laboratory water bath cleaning sonicator such as L&R Ultrasonics QS140 (L&R Manufacturing Co., Kearny, N.J.); or a Honda W113 sonicator (Honda, Denshi Japan) for 20 seconds to 2 minutes, depending on explant type. After the brief sonication step, explants are drained of originating inoculum and transferred to fresh PLANTCONs each containing 5 ml of INO media and one piece of filter paper, usually within several hours after commencement of transfection. Explants are then incubated in a lighted chamber (generally 16 hours of light at ≥5 uE) at approximately 23 to 28 C for 1 to 5 days. A series of transient GUS expression studies showed that an inoculum $OD_{660}$ of 0.3-0.8 yielded a comparatively higher proportion of meristematic transformation and transgene expression. Although lower and higher $OD_{660}$ measurements also result in successful experimental outcomes.

TABLE 1

Composition of inoculation medium.

| Ingredient | Amount/L |
| --- | --- |
| Magnesium sulfate (Fisher M63) | 0.1 g |
| Ammonium sulfate (Fisher A702) | 53.6 mg |
| Sodium phosphate monohydrate (Fisher S369-500) | 60 mg |

TABLE 1-continued

Composition of inoculation medium.

| Ingredient | Amount/L |
| --- | --- |
| Calcium chloride (Sigma C-3881) | 60 mg |
| Boric acid (Fisher A73-3) | 0.3 mg |
| Manganese sulfate (Sigma I-2550) | 1 mg |
| Zinc sulfate heptahydrate (Sigma Z-1001) | 0.2 mg |
| Potassium iodide (Sigma P-8166) | 0.075 mg |
| Sodium Molybdate dihydrate (Sigma S-6646) | 0.025 mg |
| Cupric sulfate (Fisher C493-500) | 2.5 µg |
| Cobalt chloride hexahydrate (Sigma C-2911) | 2.5 µg |
| Sequestrene (Ciba 964603) | 2.8 mg |
| Potassium nitrate (Sigma P-8291) | 1 g |
| Glucose (Phytotech G386) | 30 g |
| MES (Sigma M8250) | 3.9 g |
| Bring volume to 1 L with de-ionized distilled water | |
| pH with KOH to | 5.4 |
| Autoclave | |
| Add sterile vitamin stock containing the following | |
| Myo-inositol (Sigma I-3011) | 10 mg |
| Nicotinic acid (Sigma N-0765) | 0.1 mg |
| Pyridoxine HCl (Sigma P-8666) | 0.1 mg |
| Thiamine HCl (Sigma T-3902) | 1 mg |

Example 2

Transformation of Soybean Explants—Treatment with Cytokinin

For *Agrobacterium*-mediated transformation of soybean, an inoculum was prepared of strain ABI (C58) harboring a binary vector, such as pMON96999 containing a gus marker gene and an aadA gene conferring resistance to spectinomycin, pMON101343 containing CP4 EPSPS and GUS genes, or pMON77404 containing a gfp marker gene and a gene encoding CP4 EPSPS conferring tolerance to glyphosate, or pMON73737 containing a gfp marker gene and a DMO gene conferring tolerance to dicamba.

pMON96999 (FIG. 2) contains the uidA gene under the control of an enhanced CaMV35S promoter (U.S. Pat. Nos. 5,322,938; 5,352,605; 5,359,142; and 5,530,1960, a 35S leader sequence, and a 3' non-translated region of the nopaline synthase gene from *Agrobacterium tumefaciens* (Genbank Accession E01312), and a nuclear-targeted aadA gene for conferring resistance to spectinomycin (U.S. Pat. No. 5,217,902; (SEQ ID NO:1). The aadA adenylyltransferase gene product was targeted to the chloroplast by a chloroplast transit peptide of *Arabidopsis* EPSPS (ShkG-CTP2 Klee et al., 1987.), and was under the control of the promoter for *Arabidopsis* elongation factor EF-1alpha (Tsf1; US Patent Application 20050022261) with an FMV-35S enhancer, a Tsf1 leader (exon 1), a Tsf1 intron, and a 3' non-translated region of the pea rbcS2.

Addition of a cytokinin, thidiazuron (TDZ) or BAP at several concentrations, was tested during inoculation/co-cultivation, as well as after. After inoculation, co-cultivation was carried out for about 2-5 days (e.g. 3 days) in a Percival incubator at about 23° C. with a 16 hour light/8 hour dark photoperiod (light intensity≥5 µE). Thus the response of explants to the cytokinin was tested, and the effects of the different treatments on multiple shoot induction and transgenic event production were evaluated.

A. Effects of Cytokinin Treatment with Use of Glyphosate or Dicamba as Selective Agent.

For TDZ treatment during inoculation and co-cultivation, the soybean explants were inoculated with *Agrobacterium* strain ABI harboring pMON77404 (containing genes encoding CP4 EPSPS and GFP), or pMON101343 (containing CP4 EPSPS and GUS), and co-cultivated with the inoculum supplemented with different levels of the cytokinin for 3 days. After co-cultivation, the explants were transferred to the selection medium (WPM; Table 2) containing 200 mg/L each of carbenicillin and cefotaxime, 100 mg/L Timentin to inhibit growth of *Agrobacterium* and other contaminants, and 75 μM glyphosate or 0.01 mg/L dicamba for selection. About twenty-three to thirty days later, the explants were examined under a microscope equipped with a filter set for detecting GFP-expressing tissue, or examined for GUS expression, as appropriate. As shown in Table 3, more explants treated with TDZ had developed GFP-expressing buds or young shoots compared with untreated explants. The effect is concentration-related. In this instance, the selectable marker that was utilized conferred tolerance to glyphosate.

TABLE 2

Composition of WPM used for soybean transformation with glyphosate selection; for dicamba selection, glyphosate was replaced with 0.01 mg/L dicamba.

| Ingredient | Amount/L |
| --- | --- |
| LM WPM with vitamins (Phytotech L449) | 2.41 g |
| Sucrose (Phytotech S391) | 20 g |
| Calcium gluconate (Sigma G-4625) | 1.29 g |
| With or without Clearys 3336 WP (Carlin 10-032) | 0.03 g |
| AGARGEL (Sigma A-3301) | 4 g |
| Fill water to | 1 L |
| pH | 5.6 |
| Autoclave | |
| Carbenicillin (Phytotech C346) (40 mg/mL) | 5 mL |
| Cefotaxime (Midwest NDC0039-0019-10) (50 mg/mL) | 4 mL |
| Timentin (100 mg/ml) (Duchefa T0190) | 1 ml |
| Glyphosate (0.5M) | 3 mL |

TABLE 3

Effect of TDZ treatments during inoculation and co-cultivation on development of transgenic (GFP-positive) bud/shoot development in soybean transformation using glyphosate selection.

| Exp-Trt | TDZ level in inoculation and co-cultivation medium (mg/L) | # Explants examined | # Explants with GFP+ buds/shoots[1] | Frequency |
| --- | --- | --- | --- | --- |
| 1033-1 | 0 | 200 | 27 | 13.5% |
| 1033-2 | 0.5 | 200 | 36 | 18% |
| 1033-3 | 1.0 | 200 | 48 | 24% |
| 1033-4 | 1.5 | 200 | 50 | 25% |
| 1033-5 | 2.0 | 200 | 60 | 30% |
| 1033-6 | 3.0 | 200 | 64 | 32% |

Similar results were observed when soybean explants were treated with TDZ after inoculation and co-cultivation, e.g. during the "delay" or selection phase of tissue culture.

However, additional experiments demonstrated that use of TDZ (e.g. during inoculation/co-culture) with glyphosate as the selective agent resulted in a decrease in the number of transformed rooted soybean shoots, relative to the number obtained in the absence of TDZ, as shown in Table 4.

TABLE 4

Transformation results from glyphosate selection experiments comparing different TDZ levels in inoculation/co-culture medium.

| Expt. # | TDZ for inoculation/ co-culture (mg/L) | # Explants left for harvest | Shoots harvested Total # | % Shooting Frequency | Rooted shoots Total # | % Transformed rooted shoots |
| --- | --- | --- | --- | --- | --- | --- |
| 1041 | 0 | 435 | 57 | 13.1 | 9 | 2.1 |
| | 0.5 | 456 | 21 | 4.6 | 5 | 1.1 |
| | 1 | 450 | 22 | 4.9 | 6 | 1.3 |
| 1092 | 0 | 1125 | 189 | 16.8 | 40 | 3.6 |
| | 0.5 | 1200 | 127 | 10.6 | 17 | 1.4 |
| | 1 | 1357 | 95 | 7 | 22 | 1.6 |
| 1093 | 0 | 1000 | 101 | 10.1 | 22 | 2.2 |
| | 1 | 1100 | 39 | 3.5 | 6 | 0.5 |
| | 2 | 1244 | 18 | 1.4 | 1 | 0.1 |
| 1103 | 0 | 900 | 171 | 19 | 53 | 5.9 |
| | 2 | 750 | 37 | 4.9 | 10 | 1.3 |
| | 3 | 850 | 40 | 4.7 | 5 | 0.6 |
| 1104 | 0 | 1050 | 138 | 13.1 | 48 | 4.6 |
| | 2 | 1125 | 57 | 5.1 | 10 | 0.9 |
| | 3 | 1074 | 20 | 1.9 | 8 | 0.7 |
| 1111 | 0.5 | 600 | 112 | 18.7 | 26 | 4.3 |
| | 1 | 600 | 78 | 13 | 19 | 3.2 |
| | 2 | 600 | 40 | 6.7 | 3 | 0.5 |
| 1113 | 0.5 | 1000 | 55 | 5.5 | 14 | 1.4 |
| | 1 | 1000 | 68 | 6.8 | 10 | 1 |
| | 2 | 950 | 18 | 1.9 | 5 | 0.5 |

The effect of cytokinin treatment on transformation frequency was also assessed using DNA constructs encoding tolerance to another selective agent, dicamba. pMON73737, encoding GFP and DMO genes, was utilized. After co-cultivation, the explants were cultured for 4 days on a medium containing 0.01 mg/L dicamba, with or without BAP or TDZ as shown in Table 5. Treatment with either BAP or TDZ resulted in an increase in the number of explants displaying GFP positive buds at an early stage such as 24 days after inoculation ("DAI", Table 5).

TABLE 5

Effect of BAP and TDZ treatments for 4 days after co-cultivation on development of transgenic (GFP-positive) bud development in soybean transformation using dicamba selection.

| Experiment-Treatment | Pre-treatment w/BAP or TDZ (4 Days) | # Explants examined (24 DAI) | # Explants w/GFP+ buds (%) |
| --- | --- | --- | --- |
| 906-1 | No pre-treatment | 284 | 6 (2.1%) |
| 906-2 | 1 mg/L BAP | 325 | 12 (3.7%) |
| 906-3 | 2 mg/L BAP | 336 | 11 (3.3%) |
| 906-4 | 1 mg/L TDZ | 387 | 71 (18.3%) |
| 906-5 | 2 mg/L TDZ | 383 | 53 (13.8%) |

The explants treated with TDZ did not display strong apical dominance and produced more shoots (de novo multiple shoots) as observed in various experiments. In contrast, untreated explants showed more growth of the primary shoots (the result of apical dominance) and produced fewer shoots. Those shoots also likely developed from axillary buds. Therefore, the resulting transformation frequency was lower compared with the TDZ-treated explants. However, the growth (e.g. elongation) of the shoots resulting from transformation of soybean explants undergoing selection on glyphosate or dicamba-containing media was retarded. Using glyphosate selection, the time from inoculation to subsequent transformed R1 seed harvest was about 7 months, and the time for development of transformed rooted shoots was about 10-12 weeks. Addition of a cytokinin (BAP or TDZ) with dicamba selection had no visible effect on final transformation frequencies (TFs) obtained, although it resulted in production of more GFP positive buds at an early stage as shown in Table 5.

B. Effects of Cytokinin Treatment with Use of Spectinomycin as Selective Agent

Explants were inoculated with *Agrobacterium* in inoculation media (Table 1) by sonication for 20 sec, and then cultured on co-culture medium, which is the same as inoculation medium, as described in Example 1, The medium, for both inoculation and co-culture was supplemented with 2 mg/L TDZ. Explants were co-cultured for 4 days at about 23° C., with a 16 h light/8 h dark photoperiod. After co-culture, 12 ml liquid delay medium, which is the same as the WPM medium shown in Table 2 except not solidified with Agargel and lacking a selective agent (glyphosate, dicamba or spectinomycin), was added to each PLANT-CON™ (MP Biomedicals, Solon, Ohio) containing the explants. The explants were cultured in the delay medium for 4 days (28° C., with a 16 h light/8 hr. dark photoperiod). For selection and shoot induction, the explants were transferred to the same liquid medium but with addition of different levels of spectinomycin (25-250 mg/L spectinomycin). The explants were individually implanted into the slits of the foam sponge in the PLANTCON vessel. Each vessel contained 60 ml of medium and one piece of foam sponge holding about 25 explants.

Figure 2:
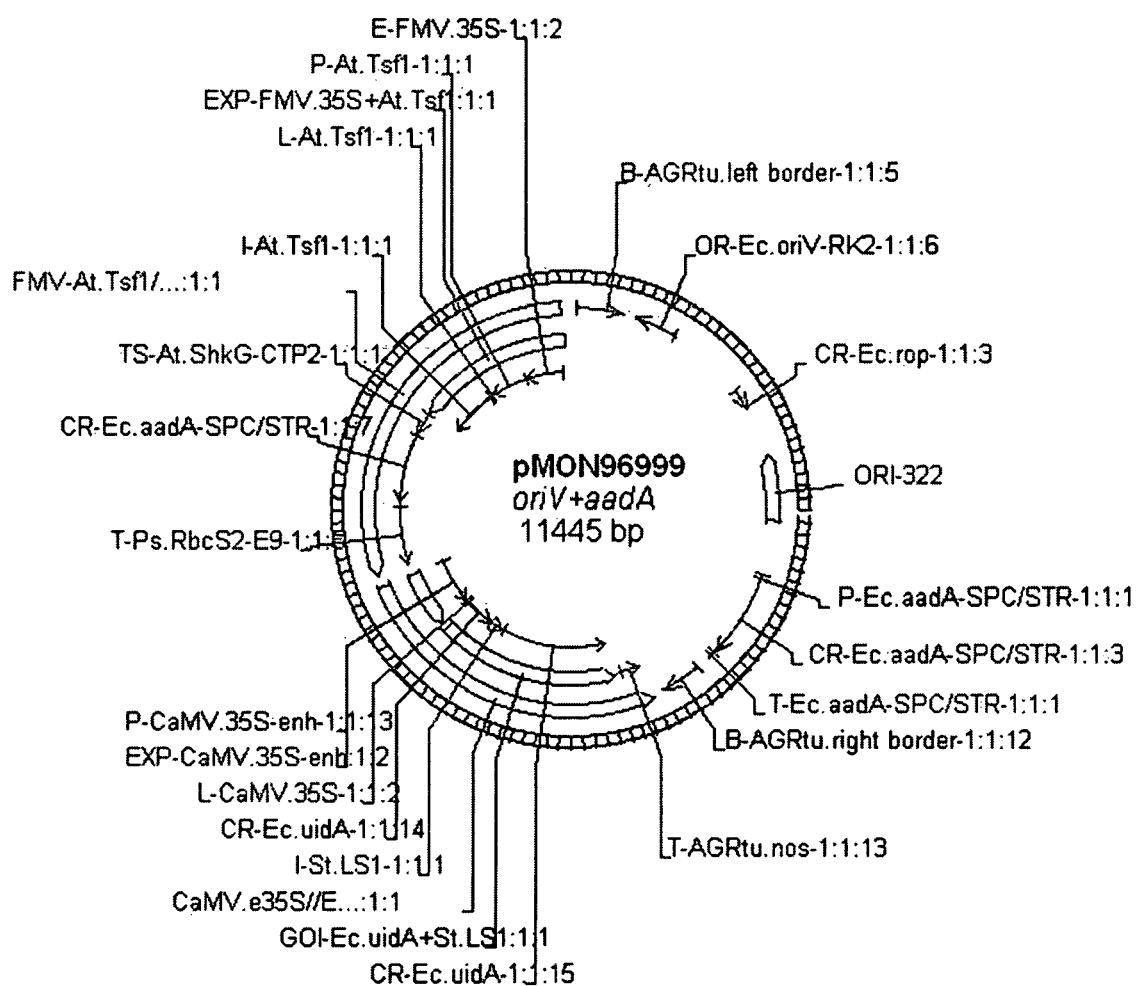
FIG. 2: Plasmid map of pMON96999.

In all treatments, the explants developed multiple buds and shoots. Samples of explants and resulting tissues were collected and assayed for GUS activity at different stages. When explant tissue transformed with an aadA gene and GUS (on pMON96999; FIG. 2) was selected in the presence of spectinomycin, distinct green (spectinomycin resistant) and bleached (spectinomycin susceptible) buds and shoots were observed, as well as GUS-positive tissues, on a large number of TDZ-treated explants approximately 3 weeks after inoculation (Table 8). Up to 80% of the explants developed GUS-positive buds and shoots within two weeks on selective medium (about 3 weeks after inoculation, i.e. about 22 DAI; Tables 8-9).

TABLE 6

Composition of *Agrobacterium* co-culture medium 1595, per L.

| Ingredient | Amount |
| --- | --- |
| TC Water | 750 ml |
| B5 stock 1 (see below) | 1 ml |
| B5 stock 2 (see below) | 1 ml |
| B5 stock 3 (see below) | 1 ml |
| B5 stock 5 (see below) | 1 ml |
| Potassium nitrate (Sigma P-8291) | 1 g |
| Glucose (Phytotech G386) | 30 g |
| MES (Sigma M-8250) | 3.9 g |
| Add TC water to 1 L | |
| TC H$_2$0 to 1000 ml | |
| pH with KOH to 5.4 | |
| Autoclave | |
| Add B5 stock 4 (see below) | 1 ml |
| B5 Stock #1 | |
| Ammonium Sulfate | 53.6 g |
| Magnesium Sulfate | 100 g |
| Sodium phosphate Monobasic | 60 g |
| B5 Stock #2 | |
| Calcium Chloride | 60 g |

TABLE 6-continued

Composition of *Agrobacterium* co-culture medium 1595, per L.

| Ingredient | Amount |
| --- | --- |
| B5 Stock #3 | |
| Boric Acid | 0.30 g |
| Manganese Sulfate | 1.0 g |
| Zinc Sulfate | 0.20 g |
| Potassium Iodide | 0.75 g |
| Sodium Molybdate | 0.025 |
| Copper Sulfate (1 mg/ml stock) | 2.5 ml |
| Cobalt Chloride (1 mg/ml stock) | 2.5 ml |
| B5 Stock #4 | |
| Thiamine HCl | 1.0 g |
| Nicotinic Acid | 0.1 g |
| Pyridoxine HCl | 0.1 g |
| Inositol | 10 g |
| B5 Stock #5 | |
| Sequestrene | 2.8 g |

A study was also conducted to evaluate if treatment with cytokinin BAP also enhanced transformation frequency for soybean transformation using spectinomycin selection by promoting multiple shoots development. Soybean explants were inoculated and co-cultured with *Agrobacterium* harboring pMON96999 (FIG. 2). The inoculation and co-culture medium were supplemented with 0, 1, 2, 3, 4 or 5 mg/L BAP. After co-culture for 3 days, the explants were cultured in a delay medium (inoculation medium lacking selection) for 4 days. The delay medium was also supplemented with the same level of BAP for each treatment as shown in Table 7. The explants were then transferred onto selection medium (the same as the delay medium but containing 150 mg/L spectinomycin) for shoot induction and selection. Explants in the treatment without BAP showed more apical dominance with more elongated primary shoots.

To determine how many explants could develop transformed shoots without BAP treatment, explant tissues were assayed for GUS activity at 42 days after inoculation. Approximately 18% of the explants had GUS+ buds or small shoots (Table 7). Most of them were axillary, and some of them were apparently chimeric. The explants treated with BAP had much less or non-elongated primary shoots, and more de novo shoots. Many of the shoots elongated on the selection medium and were harvested to induce roots on the root induction medium also containing 150 mg/L spectinomycin as in protocol "A". Transformation frequency (TF) were determined based on number of rooted shoots and were shown in Table 7. Since there was only 18% of the explants among the explants not treated with BAP that showed GUS+ buds or shoots, a TF much lower than 18% would be expected if the explants were not sacrificed for the GUS assay, since not all those GUS+ buds/shoots would continuously develop to eventually become plants. Therefore, the data strongly suggested that BAP treatment enhanced TF by inhibiting apical dominance and promoting multiple shoot development.

TABLE 7

Effect of BAP treatment during co-culture and post co-culture delay stage.

| Exp-Trt# | BAP in co-culture & 4-d post co-culture delay medium (mg/L) | # Explants left | # Explants producing GUS+ axillary buds/shoots (42 DAI) | # Rooted plants[2] | % TF |
|---|---|---|---|---|---|
| 1118-1[1] | 0 | 352 | 65 (18.5%) | n/a | n/a |
| 1118-2 | 1 | 395 | n/a | 103 | 26.1 |
| 1118-3 | 2 | 347 | n/a | 94 | 27.1 |
| 1118-4 | 3 | 350 | n/a | 87 | 24.9 |
| 1118-5 | 4 | 435 | n/a | 132 | 30.3 |
| 1118-6 | 5 | 436 | n/a | 116 | 26.6 |

[1]All the explants in this treatment were assayed for GUS activity 42 days after inoculation.
[2]Rooted in medium containing 150 mg/L spectinomycin.

TABLE 8

Effect of treatments with different levels of TDZ during inoculation and co-culture on development of GUS-positive buds.

| TDZ level for inoculation & co-culture | # Explants assayed for GUS | # Explants w/GUS+ buds (13 DAI) | % Explants with GUS+ buds (13 DAI) |
|---|---|---|---|
| 0.5 mg/L | 96 | 18 | 18.8 |
| 1.0 mg/L | 96 | 34 | 35.4 |
| 2.0 mg/L | 96 | 48 | 50.0 |

TABLE 9

Percent of explants cultured on medium containing different levels of spectinomycin that developed GUS-expressing buds and shoots.

| Experiment-treatment | Spectinomycin level used | # Explants assayed | # Explants with GUS+ shoots/buds | % |
|---|---|---|---|---|
| 1102-1 | 25 | 25 | 13 | 52 |
| 1102-2 | 50 | 25 | 18 | 72 |
| 1102-3 | 100 | 25 | 19 | 76 |
| 1102-4 | 150 | 25 | 18 | 72 |
| 1102-5 | 200 | 25 | 20 | 80 |
| 1102-6 | 250 | 25 | 20 | 80 |

Various levels of TDZ were also found to be effective in promoting development of GUS positive buds. In contrast to studies performed using glyphosate or dicamba as a selective agent, green spectinomycin-resistant shoots elongated well, and shoot harvest could be performed by six weeks after inoculation. Most cultured explant material produced one elongated shoot at a time, although some produced more than one shoot. One elongated shoot was harvested from each transformed explant. Shoot harvest stopped approximately 9 weeks after inoculation, although even more elongating shoots were being produced from additional explants. Shoots were rooted in a root induction medium (BRM). This medium contained ½ strength of MS salts, MS vitamins, 100 mg/l inositol, 100 mg/l cysteine, 30 mg/l sucrose and 100 mg/l ticarcillin and was solidified with 8 g/l washed agar and also supplemented with 150 mg/L spectinomycin and 0.1 mg/L IAA or 0.25 mg/L IBA as rooting hormone. Spectinomycin was employed at 0-250 ppm, and up to 1000 ppm in some studies. As shown in Table 10, in the first study the average transformation frequency was 18.6%, ranging from 12.6-26.1%, a significant increase from the approximate 2% transformation frequency seen in comparable experiments utilizing glyphosate as selective agent. A later study confirmed the result (Table 10). Such high transformation frequency was found with a wide range of spectinomycin concentrations (25-250 mg/L and up to 1000 mg/L), and 150 mg/L of spectinomycin was typically used in later studies. Additionally, of the first 32 plants tested to confirm transformation, 31 plants were later shown to be transformed, with only one "escape."

TABLE 10

Transformation frequency using spectinomycin selection.

| Experiment-Treatment | Spec level (mg/L) | # Explants left for shoot harvest | Shoots harvested[1] | | Plants tested for transformation | |
|---|---|---|---|---|---|---|
| | | | Total | % SF | Total | % TF |
| 1102-1 | 25 | 100 | 46 | 46 | 19 | 19 |
| 1102-2 | 50 | 216 | 101 | 46.8 | 48 | 22.2 |
| 1102-3 | 100 | 175 | 36 | 20.6 | 22 | 12.6 |
| 1102-4 | 150 | 111 | 39 | 35.1 | 29 | 26.1 |
| 1102-5 | 200 | 188 | 53 | 28.2 | 27 | 14.4 |
| 1102-6 | 250 | 200 | 55 | 27.5 | 39 | 19.5 |
| Total | | 990 | 330 | 33.3 | 184 | 18.6 |
| 1119-1 | 50 | 600 | 149 | 24.8 | 88 | 14.7 |
| 1119-2 | 100 | 600 | 123 | 20.5 | 94 | 15.7 |
| 1119-3 | 150 | 600 | 125 | 20.8 | 110 | 18.3 |
| 1119-4 | 200 | 600 | 91 | 15.2 | 75 | 12.5 |
| 1119-5 | 250 | 600 | 108 | 18.0 | 98 | 16.3 |
| Total | | 3000 | 596 | 19.9 | 465 | 15.5 |

[1]Only one shoot was harvested from each explant, although some explants produced multiple shoots. Since shoot elongation was not uniform, shoot harvest was stopped 9 weeks after inoculation although more shoots could be harvested later.
"SF" = shoot frequency; "TF" = transformation frequency Using spectinomycin selection, the time from inoculation to the time for development of transformed rooted shoots was about 8 weeks, and subsequent transformed $R_1$ seed harvest was typically <6 months.

Example 3

Figure 3:
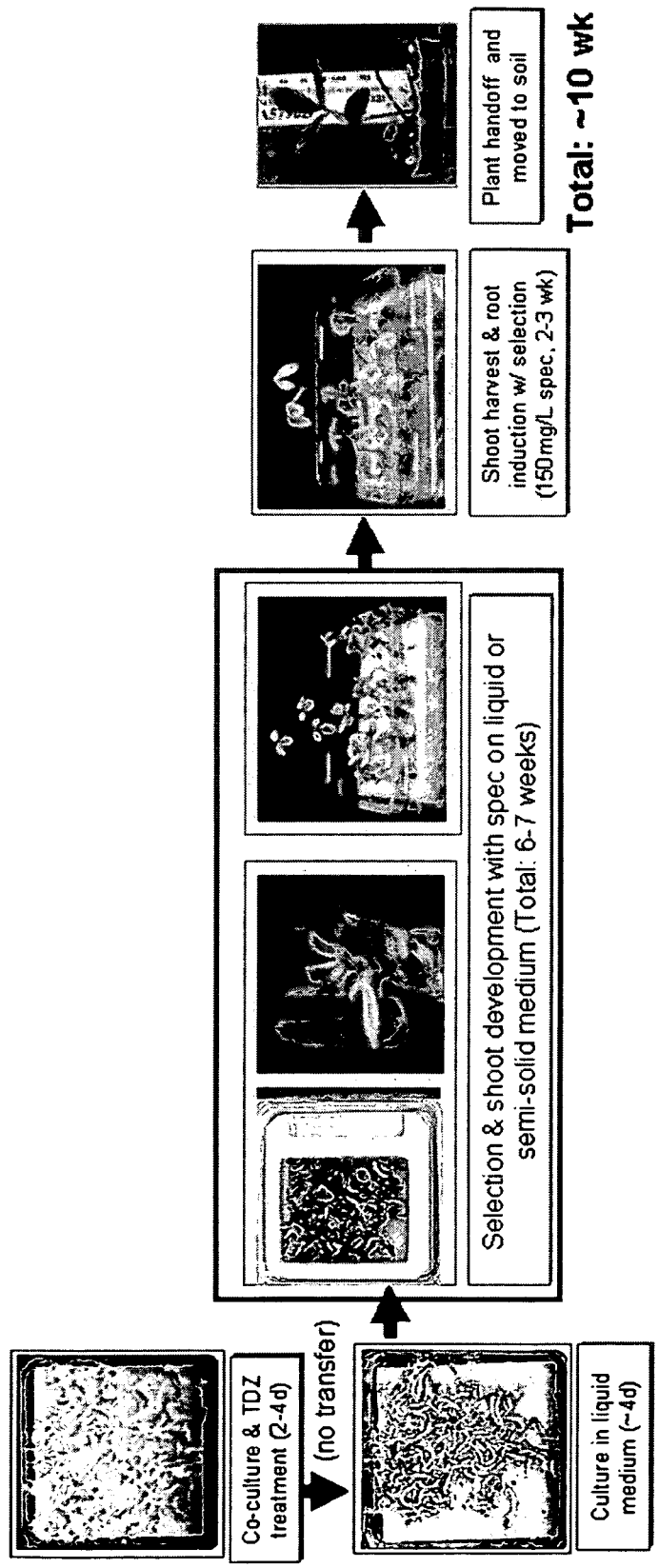
FIG. 3: Outline of spectinomycin selection protocol "A". Selection, shoot induction and elongation on liquid or semi-solid medium; rooting detached shoots on semi-solid medium.
Figure 4:
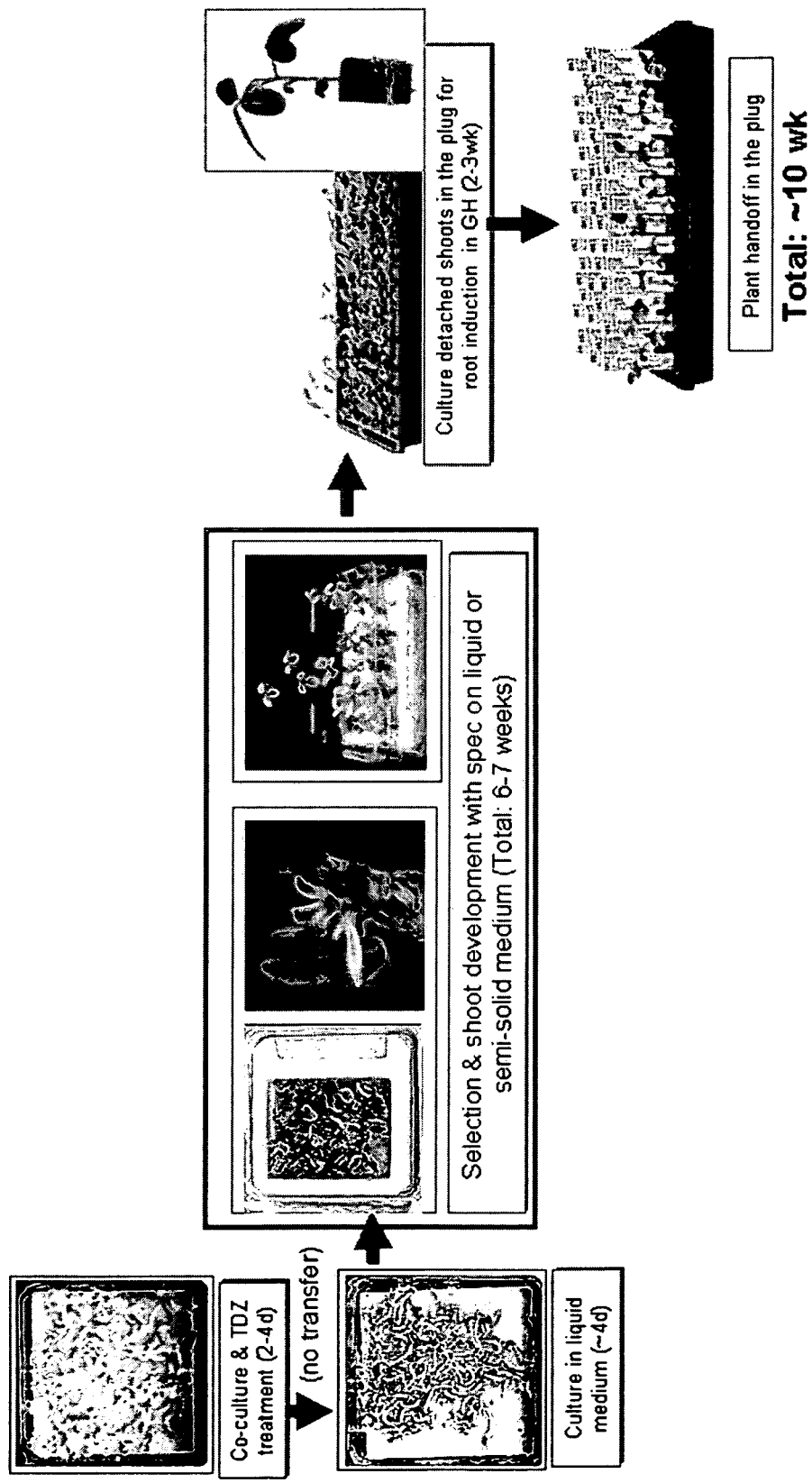
FIG. 4: Outline of spectinomycin selection protocol "B". Selection, shoot induction, and elongation on liquid or semi-solid medium; rooting detached shoots in OASIS plugs with liquid medium without selection.
Figure 5:
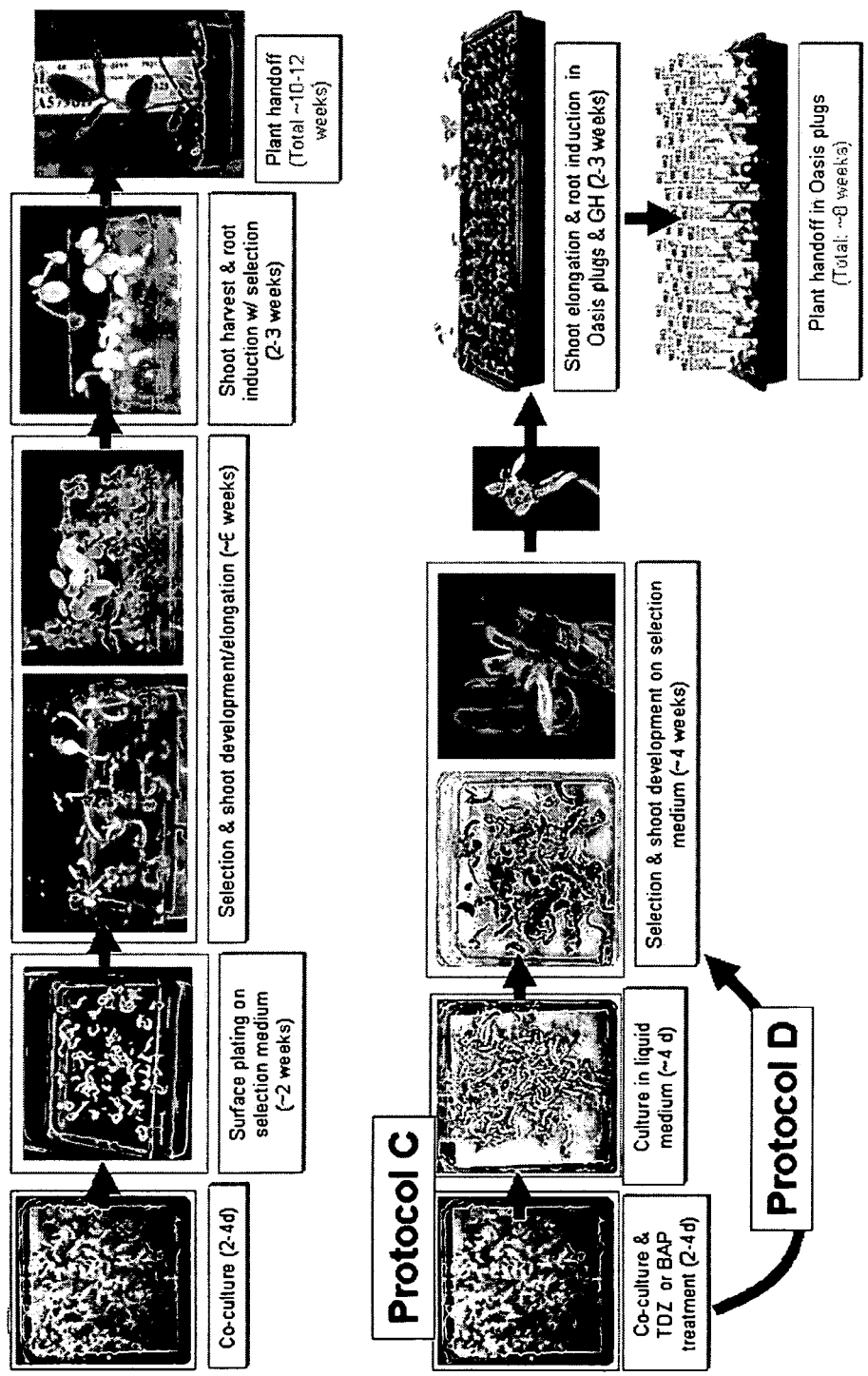
FIG. 5: Outline of spectinomycin selection protocols "C" and "D" (bottom), and comparison with protocol for selection using glyphosate (top). For Protocol "C," after co-culture the explants are retained in the original PLANT-CONs and 12 ml of liquid selection medium is added. Four days later, they are transferred onto semi-solid selection medium for selection and shoot induction. For Protocol "D," after co-culture, the explants are directly transferred onto the semisolid medium for selection and shoot induction. In both protocols "C" and "D", the explants producing green shoots are moved to Oasis® plugs with liquid medium without selection for shoot elongation and root induction. For protocol using selection with glyphosate (top), wherein shoot induction, and shoot elongation is on semi-solid medium with selection, rooting of detached shoots is also performed on semi-solid medium with selection.
Figure 6:
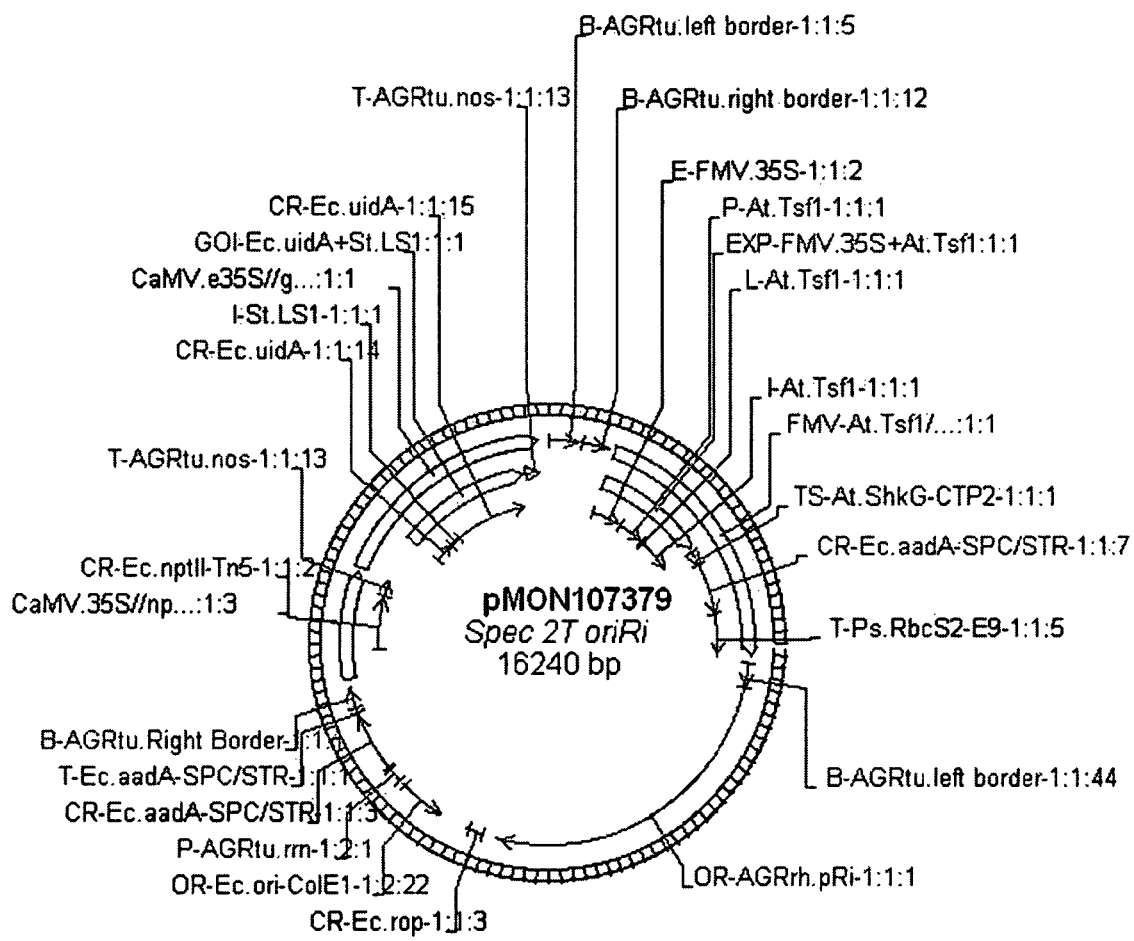
FIG. 6: Plasmid map of pMON107379 comprising 2 T-DNAs, OriRi, and aadA.

Development and Comparison of Rapid Efficient Soybean Transformation and Culture Protocols Using Spectinomycin Selection In order to improve the speed and efficiency of soybean transformation using spectinomycin selection, including with cytokinin treatment, several protocols utilizing spectinomycin selection were compared among each other and with a previously employed method that used glyphosate as the selective agent. Table 11 and FIGS. 3-5 outline protocols used and results obtained. As noted, the spectinomycin selection protocols demonstrated a high frequency of transformation, and a shorter period of time needed to complete each protocol (inoculation to next generation seed), as compared with the glyphosate selective protocol. Additional benefits include simplicity, reduced ergonomic impact, and streamlined plant handling, leading to lower costs.

The increased frequency in obtaining transgenic plants (~>10× more efficient compared to glyphosate or dicamba selection) enables an efficient 2 T-DNA transformation system and method for stacking traits by transformation into, for example, a ROUNDUP READY® germplasm followed by selection of marker-free segregants of the second gene of interest. Because many soybean breeding lines are themselves glyphosate tolerant, delivering an additional trait into such a genetic background provides a significant advantage in trait integration.

TABLE 11

Comparison of glyphosate selection protocol with exemplary spectinomycin selection protocols.

| Step | CP4 Selection protocol | Spectinomycin selection- Protocol A | Spectinomycin selection- Protocol B | Spectinomycin selection- Protocol C | Spectinomycin selection- Protocol D |
|---|---|---|---|---|---|
| Explant preparation | Seed imbibition, explant excision as noted above and in U.S. Patent Publication 20050005321 | | | | |
| Inoculation/ co-culture | Bulk sonication | Bulk sonication or sonicated in individual PLANTCON with TDZ or BAP for multiple shoot induction | Bulk sonication or sonicated in individual PLANTCON with TDZ or BAP for multiple shoot induction | Bulk sonication or sonicated in individual PLANTCON with TDZ or BAP for multiple shoot induction | Bulk sonication or sonicated in individual PLANTCON with TDZ or BAP for multiple shoot induction |
| Post co-culture stage I (shoot induction/selection) | Surface-plate explants on semi-solid selection medium (WPM + CCT (carbenicillin, cefotaxime, and ticarcillin) + 75 µM glyphosate) ~2 weeks | Add 12 ml liquid medium WPM + CCT with or without spectinomycin (150 mg/L) into the co-culture PLANTCON to inhibit *Agrobacterium* and start selection process if spectinomycin is included ~4 days | Add 12 ml liquid medium WPM + CCT with or without spectinomycin (150 mg/L) into the co-culture PLANTCON to inhibit *Agrobacterium* and start selection process if spectinomycin is included ~4 days | Add 12 ml liquid medium WPM + CCT with or without spectinomycin (150 mg/L) into the co-culture PLANTCON to inhibit *Agrobacterium* and start selection process if spectinomycin is included ~4 days | Surface-plate explants on semi-solid selection medium (WPM + CCT + spectinomycin) ~4 weeks |
| Post co-culture Stage II (shoot induction and elongation/selection) | Transfer explants to fresh semi-solid selection medium (WPM + CCT + 75 µM glyphosate); implanting ~5-6 weeks | Surface-plating or implanting explants on semi-solid selection medium; or implanting explants into foam sponge with slits or in float on liquid selection medium (WPM + CCT + spec); ~6-7 weeks. | Surface-plating or implanting explants on semi-solid selection medium; or implanting explants into foam sponge with slits or in float on liquid selection medium (WPM + CCT + spec); ~6-7 weeks. | Surface-plating or implanting explants on semi-solid selection medium; or implanting explants into foam sponge with slits or in float on liquid selection medium (WPM + CCT + spec); 4 weeks or longer | n/a |
| Post co-culture Stage III (rooting, or shoot elongation & rooting) | Detach and culture elongated shoots in semi-solid root induction medium w/glyphosate for root induction and selection. ~2-3 weeks in light culture room | Detach and culture elongated shoots in semi-solid root induction medium w/spec for root induction and selection. 2-3 weeks in light culture room | Detach and culture elongated shoots in Oasis plugs w/simple liquid medium w/o selection.; 2-3 weeks in greenhouse | Grow explants w/green shoots in Oasis plugs for shoot elongation and root induction from original radicals in simple liquid medium w/o selection. 2-3 weeks in greenhouse | Grow explants w/green shoots in Oasis plugs for shoot elongation and root induction from original radicals in simple liquid medium w/o selection. 2-3 weeks in greenhouse |
| Total duration from inoculation to obtaining plant | 10-12 weeks | 9-11 weeks | 9-11 weeks | ~8 weeks | ~8 weeks |
| Comparison with previous glyphosate selective protocol | Glyphosate inhibits apical dominance and promotes axillary bud/shoot development; Non-visual marker. Putative transgenic shoots elongate | Cytokinin (TDZ or BAP) is used during inoculation/co-culture to induce de novo multiple shoots. Visual selection: green resistant putatively transformed buds/shoots vs. white susceptible shoots; white buds/shoots stop growth at early stage. | | | |
| Comparison with previous glyphosate selective protocol-benefit | n/a | Higher transformation frequency (~10X) | Higher TF (~10X); simplify plant handling system and reduce labor and material cost in greenhouse. | Higher TF (>10X); shorter cycle; simplify transformation and the plant handling system and reduce labor and material cost in a transformation laboratory and greenhouse; reduce ergonomic stress in transformation laboratory and greenhouse. | Higher TF (>10X); shorter cycle; more simplified transformation and plant handling system and reduce labor and material cost in transformation laboratory and greenhouse; reduce ergonomic stress in transformation laboratory and greenhouse. |

Tables 12-13 demonstrate transformation frequencies obtained using Protocol C or D.

TABLE 12

Soybean transformation frequency using spectinomycin selection, Protocol "C".

| Exp-Trt | Construct (pMON) | # Ex-plants | # Ex-plant to the plug | % Ex-plants to the plug | # Plant handed off | % TF |
|---|---|---|---|---|---|---|
| 1207-2 | 96999 (1T) | 227 | 144 | 63.4 | 70 | 30.8 |
| 1207-4 | 96999 (1T) | 129 | 89 | 69.0 | 47 | 36.4 |
| 1208-3 | 96999 (1T) | 127 | 83 | 65.4 | 30 | 23.6 |
| 1208-6 | 96999 (1T) | 192 | 137 | 71.4 | 46 | 24.0 |
| 1216-1 | 96999 (1T) | 273 | 166 | 60.8 | 83 | 30.4 |
| 1216-2 | 96999 (1T) | 97 | 70 | 72.2 | 54 | 55.7 |
| Total | | 1045 | 689 | 65.9 | 330 | 31.6 |
| 1223-1 | 107379 (2T; OriRi) | 293 | 188 | 64.2 | 82 | 28.0 |
| 1223-2 | 107379 (2T; OriRi) | 292 | 167 | 57.2 | 65 | 22.3 |
| 1223-3 | 107379 (2T; OriRi) | 254 | 165 | 65.0 | 71 | 28.0 |
| 1223-4 | 107379 (2T; OriRi) | 275 | 191 | 69.5 | 72 | 26.2 |
| Total | | 1114 | 711 | 63.8 | 290 | 26.0 |

TABLE 13

Soybean transformation frequency using spectinomycin selection, Protocol "D".

| Exp-Trt | Construct (pMON) | # Ex-plants | # Ex-plant to the plug | % Ex-plants to the plug | # Plant handed off | % TF |
|---|---|---|---|---|---|---|
| 1224-1 | 107379 (2T; OriRi) | 338 | 208 | 61.5 | 74 | 21.9 |
| 1224-2 | 107379 (2T; OriRi) | 234 | 140 | 59.8 | 50 | 21.4 |
| 1225-1 | 107379 (2T; OriRi) | 235 | 173 | 73.6 | 60 | 25.5 |
| 1225-2 | 107379 (2T; OriRi) | 253 | 178 | 70.4 | 65 | 25.7 |
| 1226-1 | 107379 (2T; OriRi) | 205 | 139 | 67.8 | 49 | 23.9 |
| 1226-2 | 107379 (2T; OriRi) | 201 | 131 | 65.2 | 45 | 22.4 |
| Total | | 1466 | 969 | 66.1 | 343 | 23.4 |
| 1244-1 | 107380 (2T; OriV) | 264 | 154 | 58.3 | 61 | 23.1 |
| 1244-2 | 107380 (2T; OriV) | 205 | 124 | 60.5 | 50 | 24.4 |
| 1254-1 | 107380 (2T; OriV) | 283 | 232 | 82.0 | 111 | 39.2 |
| 1254-2 | 107380 (2T; OriV) | 267 | 213 | 79.8 | 88 | 33.0 |
| 1255-1 | 107380 (2T; OriV) | 202 | 136 | 67.3 | 47 | 23.3 |
| 1255-2 | 107380 (2T; OriV) | 295 | 198 | 67.1 | 94 | 31.9 |
| Total | | 1516 | 1057 | 69.7 | 451 | 29.7 |

TABLE 14

Estimates of transformation quality.

| Protocol and vector type | # Ex-plants tested | # Events pro-duced | TF (%) +/- s.e | # Events ass-ayed | % quality events | qTF % | Estimated MF TF % |
|---|---|---|---|---|---|---|---|
| Spec Protocol A-1T; OriV | 41786 | 8154 | 19.5- (0.89) | 828 | 19.1 | 3.7 (0.67) | n/a |
| Spec Protocol C-1T; OriV | 1045 | 330 | 31.6 (4.85) | 393* | 20.9 | 6.6 (1.09) | n/a |
| Spec Protocol C-2T; OriRi | 1114 | 290 | 26 (1.34) | 286 | 23.8 | 6.2 (0.37) | 1.8 |
| Spec Protocol D-2T; OriV | 1516 | 451 | 29.7 (2.69) | 433 | 20.3 | 6.0 (0.96) | 1.4 |
| Spec Protocol D-2T; OriRi | 1466 | 343 | 23.4 (0.76) | 326 | 24.2 | 5.7 (0.29) | 1.7 |
| CP4 Protocol-2T; OriV | 21351 | 589 | 2.76 (0.23) | 529 | 29.9 | 0.74 (0.08) | 0.18 |
| CP4 Protocol-2T; OriRi | 21651 | 360 | 1.66 (0.19) | 299 | 38.8 | 0.54 (0.08) | 0.24 |

*not all events included in calculating TF

The non-linkage rate for estimating MF TF values in Table 14 was based on the rate estimated by the data in Table 15. As can be seen, certain spectinomycin transformation protocols ("C", "D") yielded up to a 10-fold increase in the number of "quality events" obtained, as compared with the glyphosate selection protocol, while Protocol "A" showed a significant increase in TF and qTF as well. More than 92% of the events were confirmed as germline-transformed, based on GUS expression in $R_1$ immature soybean embryos when using any of Protocols "A", "C", or "D". This "escape" rate is comparable to that found observed from glyphosate selection protocols. The $R_0$ plants were also found to grow normally and set seeds ($R_1$ generation) well, averaging almost 200 seeds per plant from soybean plants transformed using any of protocols A-D.

TABLE 15

Estimate of non-linkage rate.

| Selection and backbone type | # Plants assayed | Non-linkage rate obtained |
|---|---|---|
| Spec OriV | 122 | ~23% |
| Spec OriRi | 157 | ~29% |
| CP4 OriV | 55 | ~24% |
| CP4 OriRi | 62 | ~44% |

Example 4

Comparison of Transformation Frequencies and Event Quality

Several of the above-described spectinomycin transformation protocols were compared among each other and with the glyphosate selection protocol for soybean transformation quality, as shown in Table 14. In the table below, "TF" refers to the number of events produced per the number of explants; "qTF" refers to the number of quality events per number of explants, wherein a quality event is defined as an event comprising one copy of the gene-of-interest and lacking backbone (vector sequence); and "MF TF" refers to the number of events with one copy of the gene-of-interest, not linked to marker, and lacking vector backbone sequence, per number of explants subjected to transformation.

Example 5

Development of Spectinomycin Transformation System for Dry-Excised Soybean Explants Methods of spectinomycin selection were utilized to transform dry-excised soybean explants, prepared as follows:

1) Dry, viable, seeds (properly stored quality soybean seed is approximately 10 to 12% internal moisture content) were rinsed with sterile water, or a solution of Sodium hypochlorite (ranging from 0 ppm to ~30,000 ppm active chlorine, including 50 ppm and 200 ppm active chlorine) for 3 to 20 minutes. Liquid was then drained. This process raises the internal moisture content to approximately 16%. Following this brief surface sanitation step, the seed internal moisture content is lowered in a commercial seed dryer with a flow of dehumidified air (temperature controlled to approximately 60 to 90 degrees F.) to less than 8% (4 to 6% generally preferred). This drying step maintains seed vigor, yet loosens the papery seed hull (seed coat) for processing ease. This lowered moisture content seed is also significantly more brittle. This brittleness is employed to properly split the seed in the dehulling mill, thus maximizing recovery of high quality explants with vigorous, intact meristems. Seed thus prepared can be stored for a significant period of time (2 years or more under proper conditions), or be used directly for further processing.

2) Properly prepared dry soybean seeds can be split, and viable meristem explants recovered using a variety of machines. One machine successful employed is a Grainman Rice Sheller (Model 64). Seeds split in this machine can then be further processed to recover the desired meristem-bearing explants in a Clipper-Cleaner modified with the proper sized screens. Explants recovered in this fast and gently process can be directly used for transformation, or can be stored until needed. Typical temperature conditions during storage can range from about room temperature to ⁻80 degrees C.

3) Following desired storage, explants were rehydrated for transformation. The types of media used for this step can be varied and included "bean germination medium" (BGM; Media Table 16), soy inoculum medium (INO; Table 1), and prepared log-phase *Agrobacterium* growth cultures (AGRO). The *Agrobacterium* growth culture was grown overnight in Lysogeny Broth (LB, also commonly referred to as Luria-Bertani Broth) to log phase, and then centrifuged and resuspended to a final optical density at 660 nm of 0.25 to 0.6. The medium used for the dilution is the same as the soy inoculum medium. Rehydration temperatures and durations also can be varied, with some experiments having explants that were soaked in one of these solutions overnight at 4° C. Other variations were made in the duration of exposure to respective hydration media, the various temperatures during this exposure, and the extent of saturation in the respective media. Exposure times tested ranged from 0 to 24 hours. Temperatures during longer exposure times (those greater than 4 hours) were done at either room temp (~26° C.), 23° C., or 4° C. Exposure times of 4 hours or less were all tested at room temperature. As an alternative to completely submerging or substantially saturating explants with liquid media during the hydration process, some treatments employed the use of moistened filter paper (enough liquid to wet, but not to saturate). This was done with filter paper moistened with either BGM or *Agrobacterium*-culture medium. Rehydration was performed in a variety of vessels, including but not limited to conical centrifuge tubes, graduated glass bottles, or a PLANTCON tissue culture container (MP Biomedicals, Irvine, Calif.).

After rehydration, explants were briefly sonicated in the presence of the appropriate *Agrobacterium* cultures as described in other examples. Co-culture was performed in lighted Percivals for generally 2 to 5 days (16 hours of light, 8 hours of dark, light intensity≥5 μE) at a temperature of approximately 23 to 25° C. Spectinomycin was applied as a selection agent either during rehydration, in co-culture steps, and/or following co-culture at 15 mg/L to 1000 mg/L. Phenotype positive shoots (plants) were routinely recovered (see Table 17).

TABLE 16

Media for soybean germination.

| Ingredients of BGM | mg/L |
|---|---|
| $NH_4NO_3$ | 240 |
| $KNO_3$ | 505 |
| $CaCl_2 \cdot 2H_2O$ | 176 |

TABLE 16-continued

Media for soybean germination.

| Ingredients of BGM | mg/L |
|---|---|
| $MgSO_4 \cdot 7H_2O$ | 493 |
| $KH_2PO_4$ | 27 |
| $H_3BO_3$ | 1.86 |
| $Na_2MoO_4 \cdot 2H_2O$ | 0.216 |
| $MnSO_4 \cdot H_2O$ | 5.07 |
| $ZnSO_4 \cdot 7H_2O$ | 2.58 |
| $FeSO_4 \cdot 7H_2O$ | 2.502 |
| KI | 0.249 |
| $Na_2EDTA \cdot 2H_2O$ | 3.348 |
| $CuSO_4 \cdot 5H_2O$ | 0.0008 |
| $CoCl_2 \cdot 6H_2O$ | 0.0008 |
| Thiamine HCl | 1.34 |
| Nicotinic Acid | 0.5 |
| Pyridoxine HCl | 0.82 |
| Bravo (75% WP) | 30 |
| Captan (50% WP) | 30 |
| Cefotaxime | 125 |
| Sucrose | 25000 |
| pH | 5.8 |

As shown in Table 17, a transformation frequency of 20-25% was obtained in several experiments, and over 10% was obtained routinely, depending on the protocol used.

TABLE 17

Transformation frequency (TF) of dry-excised soybean explants.

| Experiment-treatment number | # Explants | # Events | TF % |
|---|---|---|---|
| 1095 | 138 | 5 | 3.6 |
| 1109 | 455 | 23 | 5.1 |
| 1141-1 | 543 | 136 | 25 |
| 1141-2 | 541 | 67 | 12.4 |
| 1169-1 | 192 | 37 | 19.3 |
| 1260 | 281 | 57 | 20.3 |
| 1261 | 770 | 154 | 20 |
| 1263-1 | 235 | 14 | 6 |
| 1262-2 | 59 | 11 | 18.6 |
| 1263-2 | 159 | 21 | 13.2 |
| 1264-1 | 55 | 9 | 16.4 |
| 1265-1 | 636 | 151 | 23.7 |
| 1264-2 | 102 | 4 | 3.9 |
| 1265-2 | 101 | 13 | 12.9 |

Example 6

Cotton Transformation Using aadA as a Selectable Marker and Spectinomycin as a Selective Agent A. Preparation of *Agrobacterium* Inoculum

*Agrobacterium* strain C58 harboring a binary vector which carries 1 T or 2 T-DNA containing aadA and other GOI or screenable marker was used. The inoculum was prepared as described in Example 1.

B. Cotton Explants, Inoculation and Co-Culture with *Agrobacterium*.

Cotton embryo axes were mechanically excised from imbibed mature seeds and inoculation and co-cultured with prepared *Agrobacterium* was performed. Cotton seeds were mechanically processed to excise and isolate their meristematic tissues. In order to obtain transformable meristematic explant material, cotton seeds (e.g. from genotypes STN474 (Stoneville Pedigreed Seed Co., Stoneville, Miss.), Delta Pearl (Delta and Pine Land Co., Scott, Miss.), DP5415

(Delta and Pine Land Co.), SureGrow501 or SureGrow747 (Sure Grow Cotton Seed Company, Maricopa, Ariz.) were processed as follows to separate the embryo, comprising meristematic tissues, from the seed coat and cotyledon(s). Cotton seeds were removed from storage at 4° C. or −20° C. and brought to room temperature. Seeds were weighed out, placed into a sterile germinator unit, and surface-sterilized in 50% Clorox (sodium hypochlorite) for 5 min. Seeds are then rinsed 3 times with sterile distilled water and were hydrated in a liquid hydration medium (CSM) at 28° C. in the dark for about 18 hrs (range of 14 to 42 hours). Alternatively, the germination temperature may be lower, for instance about 23° C. The CSM medium contained 200 mg/L carbenicillin (PhytoTechnology Laboratories, Shawnee Mission, Kans.), 125 mg/L cefotaxime (Midwest Scientific, St. Louis, Mo.), 30 mg/L BRAVO 75 (Carlin, Milwaukee, Wis.) and 30 mg/L Captan 50 (Carlin). Other solutions have also successfully been used to hydrate the cotton seeds, including sterile deionized water or water containing a weak concentration of bleach (typically 50 to 1000 ppm sodium hypochlorite). Following hydration, seeds may be used immediately, or stored at refrigeration temperatures for up to a week prior to further processing.

Explants were rinsed in sterile water. About 1-60 g, e.g. 30 g, of explants was placed into the top part (upside down) of a Plantcon™ container (MP Biomedicals, Solon, Ohio) followed by addition of approximately 50 mL of the prepared *Agrobacterium* suspension, enough to cover the explants. After the Plantcon™ was closed, it was inserted into an appropriately sized holder, which was placed into a sonicator (e.g. L&R Ultrasonics QS140; L&R Manufacturing Co., Kearny, N.J.; or a Honda W113 sonicator, Honda, Denshi Japan). The sonicator was filled with about 2 L of 0.1% Triton® (e.g. Sigma 526-36-23; Sigma Chemical Co, St. Louis, Mo.). After up to 5 min of sonication, the Plantcon™ was placed securely on a shaker at about 80-100 rpm for 10 min for incubation. After inoculation, the *Agrobacterium* inoculum was removed from the Plantcon™ About 2 g of the inoculated explant tissue was transferred to a fresh Plantcon™ containing sterile filter paper and 5 mL of INO (Table 1), and the explants were spread on the medium surface to avoid clustering. The INO medium may also be supplemented with plant growth regulators such as gibberellins (GA3), auxins (NAA, IBA, IAA, 2,4-D, dicamba, etc), cytokinins (BAP, thidiazuron, dikegulac, kinetin, etc.), and the antimicrobial compounds 50 ppm Nystatin (50 mg/L), TBZ (10 mg/L), and the selection agent Spectinomycin (100 mg/L). The Plantcon™ containing inoculated explants was placed into a Percival incubator for co-cultivation at approximately 22-28° C. and a 16 hour light photoperiod for 2-5 days (light intensity≥5 µE).

C. Selection and Identification of Transgenic Events Using Spectinomycin as a Selective Agent.

Following co-cultivation, explants were transferred onto semi-solid selection medium in Plantcon™ containers by either individually implanting into the medium, or they were laid on the surface of the medium. The basal medium was a modified Lloyd & McCown Woody Plant Medium (WPM, Lloyd and McCown, 1981) and was supplemented with 200 mg/L cefotaxime, 200 mg/L carbenicillin and 100-200 mg/L spectinomycin (Table 18) with or without plant growth regulators or other additives to promote multiple shoot formation and growth.

TABLE 18

Components of medium for selection and shoot development used in cotton transformation - Modified Lloyd & McCown Woody Plant Medium supplemented with antibiotics.

| Ingredient | Amount/L |
|---|---|
| LM WPM with vitamins (Phytotech L449) | 2.41 g |
| Dextrose (Fisher D16-3) | 20 g |
| Calcium gluconate (Sigma G-4625) | 1.29 g |
| With or without Clearys 3336 WP (Carlin 10-032) | 0.03 g |
| AGARGEL (Sigma A-3301) | 4 g |
| Fill water to | 1 L |
| pH | 5.6 |
| Autoclave | |
| Carbenicillin (Phytotech C346) (40 mg/mL stock) | 5 mL (200 mg) |
| Cefotaxime (Midwest NDC0039-0019-10) (50 mg/mL stock) | 4 mL (200 mg) |
| Spectinomycin (50 mg/mL stock) | 3 mL (150 mg) |

Twenty five to 50 explants were cultured in each container. The explants were either immediately moved into light culture room (16-h light/8-h dark photoperiod, light intensity≥5 µE) with temperature set at approximately 28° C., or first into light room with temperature set at approximately 35° C., up to 40° C., for a short period of time (e.g. 3-5 days) before being moved to 28° C. Experiments comparing these two culture regimes were conducted and results suggested that treatment at 35° C. was beneficial (Table 19).

TABLE 19

Comparison of inoculation and co-culture methods for cotton transformation using spectinomycin selection.

| Exp-Trt | Inoc/co-cultivation method | Culture temperature | # explants w/ meristem | # GUS+ shoots (total # shoots assayed) | % explants producing GUS+ shoots |
|---|---|---|---|---|---|
| 1021-1 | A | 35° C., 3 d to 28° C. | 127 | 6 (7) | 4.7 |
| 1021-2 | B | 28° C. | 183 | 0 (2) | 0 |
| 1021-3 | B | 35° C., 3 d to 28° C. | 141 | 0 (2) | 0 |
| 1021-4 | A | 28° C. | 324 | 2 (2) | 0.6 |
| 1021-5 | A | 35° C., 3 d to 28° C. | 225 | 7 (9) | 3.1 |
| 1023-1 | A | 35° C., 3 d to 28° C. | 81 | 5 (7) | 6.2 |
| 1023-2 | B | 28° C. | 95 | 0 (0) | 0 |
| 1023-3 | B | 35° C., 3 d to 28° C. | 81 | 11 (13) | 13.6 |
| 1023-4 | A | 28° C. | 101 | 0 (0) | 0 |
| 1023-5 | A | 35° C., 3 d to 28° C. | 88 | 1 (3) | 1.1 |

In method A, all explants in each treatment were placed in one PLANTCON and *Agrobacterium* inoculum was added to cover the explants. The explants in the inoculum were sonicated (bulk sonication) to create wounds for *Agrobacterium* entry, for 2 min, followed by 10 min on shaker (80 rpm). Then the inoculum was removed and the explants were distributed to PLANTCONs each containing one piece of filter paper and 5 ml of inoculation medium. In method B, explants were distributed to the cover part of each PLANT-CON (approximately 100 explants per PLANTCON). Five ml of *Agrobacterium* inoculum was added, and the explants were then sonicated for 20 sec, and immediately were transferred along with the inoculum to the bottom part of a PLANTCON, which holds one piece of filter paper.

After approximately 3-4 weeks on the selection medium, resistant green shoots began to be evident on some explants, while bleached young shoots or primordia were clearly visible on others. In approximately another 2 weeks on selection medium, those explants developing green shoots were transferred to Oasis® plugs for shoot growth and root induction from the original radical in the greenhouse. The Oasis plugs were placed in a standard flat without holes and were situated in a simple liquid medium, which contained 0.5 g/L of WPM salts with vitamins (Phytotechnology Laboratories, Lenexa Kans.; stock No. L449) and 0.25 mg/L IBA, and were covered with plastic domes. Explants might also be transferred onto fresh selection medium with the same or higher concentration of spectinomycin, or with spectinomycin removed, for further selection and/or growth before being moved to the plugs. In some experiments, cotton explants were subjected to tissue culture and growth conditions essentially as described for soybean transformation, selection, and plant regeneration of Protocol "D", above. Cotton rooting medium (CRM; Table 20) might also be used to induce formation of roots.

TABLE 20

Components of Cotton Rooting Medium (CRM).

| Ingredient | Amount/L |
| --- | --- |
| MS basal salts (Phytotech M524) | 2.15 g |
| Myo-inositol (Sigma I-3011) | 0.1 g |
| Dextrose (Fisher D16-3) | 30 g |
| SBRM vitamin stock: | 2 mL |
| Glycine (Sigma G-6143): 1 g/L | |
| Nicotinic acid (Sigma N-0765): 0.25 g/L | |
| Pyridoxine HCl (Sigma P-8666): 0.25 g/L | |
| Thiamine HCl (Sigma T-3902): 0.5 g/L | |
| Cysteine (10 mg/mL) | 10 mL |
| Bring volume with deionized distilled H$_2$O | |
| pH with KOH | 5.8 |
| Bacto agar (BD 214030) | 8 g |
| Autoclave | |
| IAA (Sigma I-2886) (0.02 mg/mL) | 5 mL |
| Timentin (Duchefa T0190) (100 mg/mL) | 1 mL |
| Cefotaxime (Midwest NDC0039-0019-10) (50 mg/mL) | 4 mL |

In approximately 3-4 weeks, most of the shoots in Oasis® plugs had grown significantly and roots were also well developed. Tissues were assayed for molecular characterization by one or more molecular assay methods, e.g. Invader® assay (Third Wave™ Technologies, Madison, Wis.), PCR, or Southern hybridization. Leaf samples could also be collected from each green shoot and assayed for GUS activity while still on the selection medium and/or at later stage, if a construct containing a uidA gene were used. Spectinomycin served as a useful visual marker for early identification of transformation. Non-transformed tissues usually appeared bleached and often malformed under spectinomycin selection, whereas transformed tissues were green and properly developing. In experiments utilizing a uidA marker gene, the transformed nature of the green tissue could be confirmed by GUS expression after about 4-8 weeks on selection media. Therefore, using spectinomycin as a selection agent foregoes the labor intensive and time consuming GUS assays often used in meristem transformation systems, and provides the advantage of significantly reducing the labor involved in producing transgenic plants.

Example 7

Corn Transformation Using aadA as a Selectable Marker Gene

A. Corn Explants

Ears containing immature embryos (e.g. FBLL or LH244) are harvested approximately 10 days after pollination and kept refrigerated at 4° C. until use (up to 5 days post-harvest). The preferred embryo size for this method of transformation is ~1.0-2.0 mm. This size is usually achieved about 10 days after pollination inside the greenhouse with growth conditions of an average temperature of 87° F., day length of 14 hours with supplemental lighting supplied by GE 1000 Watt High Pressure Sodium lamps. The method is genotype independent.

B. Preparation of *Agrobacterium* Inoculum

*Agrobacterium* strain C58 harboring a binary vector which carries 1 T- or 2 T-DNA containing aadA and other GOI or screenable marker are used. The inoculum can be prepared as described in US Patent Application Publication No. 20040244075.

C. Inoculation and Co-Culture

Immature embryos are isolated from surface sterilized ears and directly dropped into the prepared *Agrobacterium* cell suspension in 1.5-mL microcentrifuge tube. The isolation lasts continuously for 15 min. The tube is then set aside for 5 min, which makes the inoculation time for individual embryos range from 5 to 20 min. After the *Agrobacterium* cell suspension is removed using a fine tipped sterile transfer pipette, the immature embryos are transferred onto co-culture medium (Table 21). The embryos are placed on the medium with the scutellum side facing up. The embryos are cultured in a dark incubator (23° C.) for approximately 24 h.

D. Selection, Regeneration and Growth of Transformants on Spectinomycin-Containing Medium After the co-cultivation, the embryos are transferred onto a modified MS medium (Induction MS, Table 21) supplemented with 500 mg/L carbenicillin and 50, 100, 150, 200, or 500 mg/L mg/L spectinomycin in Petri dishes (100 mm×25 mm), 20 to 25 embryos per plate. Auxin and cytokinin are present to initiate an embryogenic culture response from the scutellar tissue. The plates are kept in a dark culture room at 27° C. for approximately 2 weeks. Immature embryos with callus developed are transferred individually onto the first regeneration medium, the same medium mentioned above except 2,4-D and picloram are replaced by 3.5 mg/L BAP (MS/BAP, Table 21) and the carbenicillin level is reduced to 250 mg/L. The cultures are moved to a culture room with 16-h light/8-h dark photoperiod and 27° C. After 5-7 days, the callus pieces may also be transferred onto the second regeneration medium, a hormone-free MS-based medium (MSOD, Table 21) in Petri dishes (100 mm×25 mm). After approximately another 2 weeks, the callus pieces that have green shoots regenerated or are still alive are transferred onto the same hormone-free medium in Phytatrays for further selection and growth. All media mentioned above is supplemented with 50, 100, 150 or 200 mg/L spectinomycin. Regenerated green plants (R0) are moved to soil in peat pots in a growth chamber when they reach the top of Phytatrays and have one or more healthy roots. After an additional 7 to 10 days, they are then transplanted into 12-in pots and moved to greenhouse with conditions for normal corn plant growth. The plants are either self-pollinated or crossed with wild-type plants.

Molecular assays (e.g. as described above for cotton plants) are conducted to characterize the plants.

TABLE 21

Culture media for use in transforming and regenerating corn.

| Component | ½ MS VI | ½ MS PL | Co-culture medium | Induction MS | MSW50 | MS/6BA | MSOD |
|---|---|---|---|---|---|---|---|
| MS salts | 68.5 g/l | 68.5 g/l | 2.2 g/l | 4.4 g/l | 4.4 g/l | 4.4 g/l | 4.4 g/l |
| Sucrose | 20 g/l | 68.6 g/l | 20 g/l | 30 g/l | 30 g/l | 30 g/l | — |
| Maltose | — | — | — | — | — | — | 20 g/l |
| Glucose | 10 g/l | 36 g/l | 10 g/l | — | — | — | 10 g/l |
| l-Proline | 115 mg/l | 115 mg/l | 115 mg/l | 1.36 g/l | 1.38 g/l | 1.36 g/l | — |
| Casamino Acids | — | — | — | 50 mg/l | 500 mg/l | 50 mg/l | — |
| Glycine | 2 mg/l | 2 mg/l | 2 mg/l | — | 2 mg/l | — | — |
| l-Asparagine | — | — | — | — | — | — | 150 mg/l |
| myo-Inositol | 100 mg/l | 100 mg/l | 100 mg/l | — | 100 mg/l | — | 100 mg/l |
| Nicotinic Acid | 0.5 mg/l | 0.5 mg/l | 0.5 mg/l | 1.3 mg/l | 0.5 mg/l | 1.3 mg/l | 1.3 mg/l |
| Pyridoxine•HCl | 0.5 mg/l | 0.5 mg/l | 0.5 mg/l | 0.25 mg/l | 0.5 mg/l | 0.25 mg/l | 0.25 mg/l |
| Thiamine•HCl | 0.1 mg/l | 0.1 mg/l | 0.6 mg/l | 0.25 mg/l | 0.6 mg/l | 0.25 mg/l | 0.25 mg/l |
| Ca Pantothenate | — | — | — | 0.25 mg/l | — | 0.25 mg/l | 0.25 mg/l |
| 2,4-D | — | — | 3 mg/l | 0.5 mg/l | 0.5 mg/l | — | — |
| Picloram | — | — | — | 2.2 mg/l | — | — | — |
| Silver Nitrate | — | — | 1.7 mg/l | 1.7 mg/l | — | — | — |
| BAP | — | — | — | — | — | 3.5 mg/l | — |

[1]Media ½ MSVI and ½ MSPL are used as liquid. Co-culture medium is solidified with 5.5 mg/l low EEO agarose.
All other media are solidified with 7 g/l Phytagar or 3 g/l phytagel for glyphosate selection.

Example 8

Preparation of an Enhanced 16S RNA Promoter from *Agrobacterium* and CTP-aadA Fusion Genes pMON107379, a 2 T-DNA vector with OriRi replication origin has a promoter located in the backbone (i.e. outside of the T-DNA) for selection of spectinomycin resistance in *E. coli* or *Agrobacterium* host cells. To make pMON107379, the plant spec selection cassette was excised from pMON96999 (FIG. 2) with NotI digestion and inserted into pMON107341 opened with PspOMI. The parental pMON107341 is an oriRi based vector with an improved spectinomycin resistance cassette driven by P-rrn promoter. An enhanced 16S RNA promoter from *Agrobacterium* (SEQ ID NO:3) is especially useful when the copy number of the vector is low, as with vectors containing OriRi. The P-rrn promoter was isolated from the *Agrobacterium* strain C58 16S rDNA by PCR, and fused to the virE operon ribosomal binding site (RBS) to enable its efficient translation in both *E. coli* and *Agrobacterium*. pMON107379 also comprises an aadA gene that encodes an aminoglycoside-3'-adenyltransferase (SEQ ID NO:1) conferring spectinomycin resistance, the gene encoding an aminoglycoside-3'-adenyltransferase also being fused with a chloroplast transit peptide (SEQ ID NO:2) for transport of the nuclear-encoded aminoglycoside-3'-adenyltransferase to plastids.

Example 9

Direct Retransformation of Elite ROUNDUP READY™ Germplasm in Soybean and Cotton

Utilizing methods described herein, elite transgenic Round-Up Ready™ germplasm can be transformed utilizing 2 T-DNA's encoding the aadA gene for spectinomycin selection while employing a new gene (often referred as "the gene of interest") on the second T-DNA (or plasmid, if two plasmids are used) to allow segregation away from the aadA as described.

A Cotton RRFlex® seed variety (07W610F) and germplasm control non-transgenic variety (00S04) were compared. Seed was imbibed for ~18 hrs in 24° C., machine excised and machine-sieved (in two steps) following by floatation enrichment of explants. Explants were inoculated with *Agrobacterium* suspension in INO at OD$_{660}$ 0.3, sonicated for 2 min, and incubated for 10 min. The *Agrobacterium* suspension was then removed and explants distributed into co-culture containers at approximately 2 g per container. Explants were laid onto filter papers wetted with 5 ml of co-culture media (INO with additions of 50 ppm Nystatin, 10 ppm TBZ, and 100 ppm Spectinomycin) and co-cultured in a lighted Percival incubator at approximately 23 to 25° C. (16 hrs light/8 hrs dark, light intensity≥5 µE) for 3 days. Explants were then transferred onto WPM media with 150 ppm spectinomycin, incubated for 3 days in 35° C. light room (16 hrs light/8 hrs dark), and then moved to 28° C. light room (16 hrs light/8 hrs dark). Phenotype positive green plantlets were harvested 6 weeks after inoculation, placed in Oasis® plugs (Smithers-Oasis USA; Kent, Ohio) wetted with 0.5 g/L WPM salts (optionally including IBA at 0.25 mg/L to improve rooting) and moved to green house conditions. Once plants acclimatized and started to grow they were assayed for CP4, GUS, and vascular GUS expression (a predictor of germline transformation). Retransformed transgenic plants were expected to be CP4+ GUS+, while transformed control plants were expected to be CP4- GUS+. An analysis of the yield of transformed plants is listed in Table 22 below. Total transformation frequency is expected to increase, as analysis is not complete at this time. The described procedure is useful to re-transform transgenic cotton plants with an efficiency similar to transformation of a conventional non-transgenic cotton variety.

TABLE 22

Transformation frequency of retransformed germplasm.

| Cotton Germplasm | Quality explants inoculated | Spectinomycin phenotype positive (green) plantlets | % green Plantlets | Number of plants sampled for GUS | Plants expressing GUS in all leaves, (germline) | % TF, germline expressing GUS |
|---|---|---|---|---|---|---|
| 00S04 | 928 | 18 | 1.90% | 11 | 2 | 0.22% |
| 07W610F | 3665 | 87 | 2.40% | 64 | 9 | 0.25% |

Example 10

Sterilization of Seeds and/or Explant Material

A number of techniques of sterilizing seeds before excision, as well as sterilizing explants after excision from the seeds were tested. Post-excision sterilization of dry explants using chlorine gas in a vacuum desiccation chamber was tested at time intervals ranging from 15 minutes to 16 hours. Contamination control increased with longer exposure to Cl gas, although fungal contamination grew in treatments in which the exposure to Cl gas had surpassed the survivable threshold of the explants.

Ozone gas treatments were also tested. Both whole seed (before excision) and dry explants (after excision) were exposed to $O_3$ gas) in a PLEXIGLAS chamber (OSR-8 Ozone Generator; Ozone Solutions, Sioux Center, Iowa) at various time intervals of 1-24 hours. $O_3$ was used at a concentration of 467 ppm. After seed was exposed to ozone, embryonic material was excised and explant viability was measured. Ozonation of soybean seed for 12 hours or less did not impact viability of subsequently isolated explants, but drastically decreased bioburden found in explants. Ozonation of dry excised explants for as little as 1-4 hours decreased explant health (i.e. number of viable embryos).

Additional tests on pre-excision sterilization of whole seed were performed using a bleach solution of 200 ppm active chlorine, followed by an overnight hydration period (~9 hours) in a solution of 50 ppm active chlorine. These seeds were then allowed to dry in a laminar flow hood (typically for 12-48 hours) before being excised mechanically. A modification to the 50% bleach soak protocol was also tested, in which the seeds were first rinsed with a 70% solution of ethanol. The ethanol was immediately drained (total exposure to ethanol was less than 5 seconds), and then the 50% bleach soak was performed by treating seeds 3-15 min in 50% bleach followed by 3 rinses with water and drying the seeds overnight such that the moisture content was less than 8%. UV light may also be employed to sterilize the plant material.

Example 11

Hydration of Seeds and Explant Material

Studies employing new pre-culture hydration/germination strategies were tested. The types of media used for this step included "bean germination medium" (BGM; Table 16), soy inoculum medium (INO; Table 1), and prepared log-phase Agrobacterium growth cultures (AGRO). The Agrobacterium growth culture was grown overnight in Lysogeny Broth (LB, also commonly referred to as Luria-Bertani Broth) to log phase, and then centrifuged and resuspended to a final optical density at 660 nm of 0.25 to 0.6. The medium used for the dilution is the same as the soy inoculum medium. Explants were soaked in this solution overnight at 4° C. Other variations were made in the duration of exposure to respective hydration media, the various temperatures during this exposure, and the extent of saturation in the respective media. Exposure times tested ranged from 0 to 24 hours. Temperatures during longer exposure times (those greater than 4 hours) were either room temp (~26° C.), 23° C., or 4° C. Exposure times of 4 hours or less were all tested at room temperature. As an alternative to completely submerging or substantially saturating explants with liquid media during the hydration process, some treatments employed the use of moistened filter paper (enough liquid to wet, but not to saturate). This was done with filter paper moistened with either BGM or Agrobacterium-culture medium. Rehydration was performed in a variety of vessels, including but not limited to conical centrifuge tubes, graduated glass bottles, or a PLANTCON tissue culture container (MP Biomedicals, Irvine, Calif.).

This example also demonstrates that hydration can be done in a variety of media containing various types of carbohydrates such as glucose (INO), and sucrose (BGM). Other carbohydrates such as galactose may be useful in hydration medium.

Example 12

Transformation of Dry-Excised Soy Explants Stored for Extended Periods of Time

Dry-excised explants were stored for up to 20 months at −20° C. to 4° C., and then tested for survival, transformability and vigor. Explant survival and overall vigor appeared to be similar in all treatment groups, regardless of storage conditions or temperature compared to control treatment (Treatment 1). This demonstrates the ability to store dry-excised explants for almost two years without detriment. Explants from each treatment were tested for transient GUS expression 4 days after inoculation. Table 23 shows a comparison of meristem specific gus expression between treatments, scored on a scale from 0-9, with 0 being no visible expression, and 9 being extensive expression in all 3 meristems of the embryo. This demonstrates that dry-excised explants can not only survive long-term storage in various conditions without significant loss of vigor, but they also retain amenability to transformation. Thus it is now possible to excise large quantities of explants during off-peak times for later use, which represents significant potential cost savings and flexibility in planning and executing transformation studies.

TABLE 23

Effect of storage duration and temperature on explant transformation.

| Treatment | Seed Sterilization Technique | Excision technique | Storage duration | Storage temperature | Transient gus expression (scale of 0-9) |
|---|---|---|---|---|---|
| 1 & 2 | 50% bleach rinse | Automated dry excision with Grainman Rice dehuller | None | NA | 0.90, 1.60 |
| 3 | 50% bleach rinse | Automated dry excision with Grainman Rice dehuller | 17 months | 4° C. | 0.20 |
| 4 | 50% bleach rinse | Automated dry excision with Grainman Rice dehuller | 17 months | −20° C. | 0.10 |
| 5 | 50% bleach rinse | Manual dry excision | 20 months | 4° C. | 0.70 |
| 6 | 50% bleach rinse | Manual dry excision | 20 months | −20° C. | 1.50 |

Example 13

Identification of Suitable Pre-Inoculation Culture ("Pre-Culture") Compositions and Conditions It is likely that dry excised explants are still in a state of semi-dormancy when they are inoculated with *Agrobacterium* for transformation. Thus a method was developed to stimulate the metabolic activity of the dry excised explants prior to *Agrobacterium* inoculation, for increasing their transformation competency. That is, by manipulating the biology of the dry explant, it is possible to increase % germline positive events per explant by 2 to 10 fold.

Several media compositions: BGM (Table 16), INO (Table 1), or OR (Table 24) were tested at 23° C. and/or 28° C. temperatures, and under different light/dark conditions from 1 to 5 days, for their ability to enhance transformation competency. After pre-culturing step, explants were pooled together and inoculated with the *Agrobacterium* culture according to the method described in Example 1. Transient GUS expression assays performed on explants showed increased GUS activity in the pre-cultured treatments after 2 days and 4 days of co-culture.

Plant losses occurred due to fungal infection in some of the pre-culturing experiments, but overall TF of the dry excised explants that were pre-cultured on filter papers wetted with BGM at 23° C. in dark for 5 days appeared to be highest when compared with dry excised explants that were not pre-cultured. The losses due to fungal contamination could be mitigated by using an anti-fungal agent such as BRAVO 75 and Captan 50 at about 1% each during the pre-culture and/or co-culture step. Southern blot and INVADER analysis of the plants produced in this example with a CP4 probe confirmed the transgenic nature of these plants.

TABLE 24

SOY Organogenic (OR) MEDIUM

| COMPOUND: | PER 4 LITER: | |
|---|---|---|
| MS Salts | 17.2 g | |
| 3X Minor MS Salts | 40 ml | |
| Nicotinic Acid (1 mg/ml) | 4 ml | ☐ |
| Pyridoxine HCl (1 mg/ml) | 4 ml | ☐ |
| Thiamine HCl (1 mg/ml) | 46.8 ml | ☐ |
| Sucrose (Ultra Pure) | 120 g | ☐ |
| Myo-Inositol (Cell Culture Grade) | .40 g | ☐ |
| pH | 5.8 ☐ | |
| Washed Agar | 32 g ☐ | ☐ |
| ADDITIONS AFTER AUTOCLAVING: | | |
| Proline (2.5 m Stock) | 19.2 ml ☐ | ☐ |
| TSG/OR Hormone Stock | 40.0 ml ☐ | |

TABLE 25

Effect of pre-culture of dry explant; transformation frequency using pMON10343.

| Explant Type | Pre-culture Media compositions and conditions | Explants | Rooted Shoots | TF | % Fungal loss (PLANTCONs) |
|---|---|---|---|---|---|
| WET | None | 300 | 15 | 5.00% | 0% |
| DRY | None | 650 | 6 | 0.92% | 13% |
| DRY | BGM, 5 d 23 C. dark | 972 | 29 | 2.98% | 0% |
| DRY | BGM, 5 d 23 C. 16/8 light | 365 | 1 | 0.27% | 44% |
| DRY | BGM, 5 d 28 C. dark | 315 | 3 | 0.95% | 7% |
| DRY | BGM, 5 d 28 C.16/8 light | 188 | 1 | 0.53% | 62% |

Studies were repeated comparing two constructs, pMON101343, comprising one T-DNA that comprises a CP4 gene specifying glyphosate resistance and an OriV replication origin; and pMON107350 comprising one T-DNA that comprises a CP4 gene specifying glyphosate resistance and an OriR replication origin (US20070074314) in the vector backbone. Again, pre-culturing of dry explants boosted TF as compared to the TF of non pre-cultured dry explants, as shown in Table 26.

TABLE 26

Additional studies on pre-culture of dry-excised explants.

| Explant type and vector | # Explants | # Rooted Shoots | TF |
|---|---|---|---|
| pMON101343 | | | |
| WET | 535 | 16 | 2.99% |
| DRY | 1331 | 8 | 0.60% |
| DRY PRECULTURE | 2437 | 43 | 1.76% |
| pMON107350 | | | |
| WET | 671 | 11 | 1.64% |
| DRY | 190 | 0 | 0.00% |
| DRY PRE-CULTURE | 500 | 9 | 1.80% |

As shown in Table 27 pre-cultured dry excised explants also yielded higher TFs when explants were cultured in liquid regeneration medium (media of Table 12 except for AgarGel) which was removed and added automatically using a robotic system. TF appeared to be even higher with the liquid regeneration medium with a pre-culturing step. Wet excised explants in liquid media appear to have had low TF due to contamination.

Pre-culturing surprisingly improves competency for transformation and improves transformation uniformity. Such improvements are crucial to reducing variability during production runs at industrial scale for producing transgenic soybean plants.

TABLE 27

Pre-culture of dry excised explants; comparison of solid and liquid media.

| Explant type pMON101343 | Pre-culture Media compositions and conditions | Regeneration medium | Explants | Rooted Shoots | TF |
|---|---|---|---|---|---|
| WET | None | solid WPM | 460 | 17 | 3.70% |
| WET | None | liquid WPM | 31 | 0 | 0.00% |
| DRY | None | solid WPM | 1286 | 8 | 0.62% |
| DRY | None | liquid WPM | 128 | 0 | 0.00% |
| DRY | BGM, 5 d 23 C. dark | solid WPM | 1257 | 33 | 2.63% |
| DRY | BGM, 5 d 23 C. dark | liquid WPM | 111 | 3 | 2.70% |

Example 14

Production of Transgenic Soybean Plants Using Dry Soybean Explants and Spectinomycin Selection Dry, viable, seeds (properly stored quality soybean seed comprise approximately 10 to 12% internal moisture content) were rinsed with sterile water, or a solution of Sodium hypochlorite (ranging from 0 ppm to ~30,000 ppm active chlorine, including 50 ppm and 200 ppm active chlorine) for 3 to 20 minutes. Liquid was then drained. This process raises the internal moisture content to approximately 16%. Following this brief surface sanitation step, the seed internal moisture content was lowered in a commercial seed dryer with a flow of dehumidified air (temperature controlled to approximately 60 to 90 degrees F.) to less than 8%.

Following desired storage, explants were rehydrated for transformation. The types of media used for this step may be varied and included "bean germination medium" (BGM; Table 16), soy inoculum medium (INO; Table 1), and prepared log-phase *Agrobacterium* growth cultures (AGRO). The *Agrobacterium* growth culture was grown overnight in Lysogeny Broth (LB, also commonly referred to as Luria-Bertani Broth) to log phase, and then centrifuged and resuspended to a final optical density at 660 nm of 0.25 to 0.6. The medium used for the dilution is the same as the soy inoculum medium. Rehydration temperatures and durations also can be varied, with some experiments having explants that were soaked in one of these solutions overnight at 4° C. Other variations were made in the duration of exposure to respective hydration media, the various temperatures during this exposure, and the extent of saturation in the respective media. Exposure times tested ranged from 0 to 24 hours. Temperatures during longer exposure times (those greater than 4 hours) were done at either room temp (~26° C.), 23° C., or 4° C. Exposure times of 4 hours or less were all tested at room temperature. As an alternative to completely submerging or substantially saturating explants with liquid media during the hydration process, some treatments employed the use of moistened filter paper (enough liquid to wet, but not to saturate). This was done with filter paper moistened with either BGM or *Agrobacterium*-culture medium. Rehydration was performed in a variety of vessels, including but not limited to conical centrifuge tubes, graduated glass bottles, or a PLANTCON tissue culture container (MP Biomedicals, Irvine, Calif.).

After rehydration, explants were briefly sonicated in the presence of the appropriate *Agrobacterium* cultures. Co-culture and subsequent steps were performed in lighted Percival incubators for 2 to 5 days (16 hours of light, 8 hours of dark, with light intensity of about 5 μE to 200 μE) at a temperature of approximately 23 to 25° C., and may be performed up to about 35° C. Light is known to promote gene transfer from *Agrobacterium* to plant cells. Spectinomycin was applied as a selection agent either during rehydration, in co-culture steps, and/or following co-culture at 15 mg/L to 1000 mg/L.

Phenotype positive shoots (plants) were routinely recovered, as shown in Table 28, using the construct, pMON96999, comprising one T-DNA comprising an aadA gene and an OriV origin of replication or the construct, or pMON101343 comprising one T-DNA comprising a CP4 gene and an OriV origin of replication. By "phenotype positive" in the presence of spectinomycin, it is meant that shoots are green and robust, while phenotype negative shoots are weak and bleached (white), if they elongate at all. Spectinomycin or glyphosate were used in the regeneration medium (both sold or liquid) at the concentration shown in Table 28.

TABLE 28

Transformation frequency of dry soybean explants using glyphosate or spectinomycin as selective agent.

| Spectinomycin (% TF) | | | | Glyphosate (% TF) |
|---|---|---|---|---|
| 25 ppm | 50 ppm | 100 ppm | 200 ppm | 50 uM |
| 4.66 | 4.24 | 6.34 | 5.99 | 2.00 |

Spectinomycin was also used as a selective agent for transformation of dry excised soybean embryos utilizing the following conditions: 1 hr hydration in INO medium, 4 days co-culture in INO, 150 ppm spectinomycin, with culture on solid or liquid WPM (Table 2; with or without added agar). Temperatures of 23-25 or 28° C., up to about 35° C., may be utilized. Phenotype positive shoots were harvested at 8 and 10 weeks post *Agrobacterium* inoculation, and rooting was induced on solid BRM (see Example 2) with 150 ppm Spectinomycin. Very high transformation frequencies of 25.05% and 19.27% were obtained in two different studies.

Example 15

Production of Transgenic Soybean Plants Using Dry Soybean Embryos, Spectinomycin, and Liquid Culture Medium In these studies, explants were initially hydrated and eventually regenerated on WPM solid media with liquid overlay or WPM liquid medium as above. All explants were transferred at 6 weeks post inoculation to trays containing Oasis® Wedge System (Smithers-Oasis USA; Kent, Ohio) and a simplified liquid medium (0.5 g/L WPM with 0.25 mg/L IBA). Rooted and shooted R₀ plants were obtained two to 4 weeks later. In all studies and treatments, initial hydration of explants was done for 1 hour in the respective media as shown in the Table 29. Liquid culture medium was the same as in Table 2 except glyphosate was replaced by spectinomycin at 150 ppm. In liquid overlay treatment both solid and liquid culture media were used; liquid medium was dispensed over the top of explants as they were lying on solid medium at a specified time during tissue culture as identified in the Table 30. This was done as a type of media refreshment and avoids the need for transferring explants from old media to new media. In the control treatments, explants were surface plated on a solid WPM medium (Table 2). Shoots were harvested and rooted on solid BRM as described above, except glyphosate was replaced with spectinomycin at 150 ppm.

TABLE 29

Transformation frequency with given hydration conditions.

| Treatment | Hydration medium | Incubation with *Agrobacteria* | TF % (mean of 3 repeats) |
|---|---|---|---|
| 1 - Control | INO | 0 minutes | 3.10% |
| 2 | BGM w/o cefotaxime | 0 minutes | 14.67% |

TABLE 29-continued

Transformation frequency with given hydration conditions.

| Treatment | Hydration medium | Incubation with *Agrobacteria* | TF % (mean of 3 repeats) |
|---|---|---|---|
| 3 | BGM w/o cefotaxime | 15 minutes | 15.45% |
| 4 | BGM w/o cefotaxime | 30 minutes | 18.50% |
| 5 | INO | 0 minutes | 13.98% |
| 6 | INO | 15 minutes | 9.64% |
| 7 | INO | 30 minutes | 13.79% |

TABLE 30

Liquid overlay timing.

| Treatment | Liquid overlay timing | Liquid medium overlay volume on solid WPM | Oasis® Wedge transfer for regeneration | TF % (mean of repeats) |
|---|---|---|---|---|
| Control - 1 | NA | None | No | 8.00% |
| 2 | None | None | Yes | 14.67% |
| 3 | 3 weeks post inoculation | 5 mLs | Yes | 15.45% |
| 4 | 3 weeks post inoculation | 10 mLs | Yes | 18.50% |
| 5 | 4 weeks post inoculation | 5 mLs | Yes | 13.98% |
| 6 | 4 weeks post inoculation | 10 mLs | Yes | 9.64% |

Example 16

Production of Transgenic Soybean Plants Using Dry Soybean Embryos, Spectinomycin, and Transferring the Whole Regenerated Explant with a Pre-Culturing Step In these studies, as with Example 13, a pre-culturing step (5 days 23° C. dark in BGM) was used. A one hour hydration of the dry excised explant on INO medium was also done before the pre-culturing step. About 12 mls of liquid WPM containing 150 ppm of spectinomycin was dispensed directly into the co-culture PLANTCON after the co-culture period, and explants were surface plated on solid WPM containing 150 ppm spectinomycin 4 days later. In this example, phenotype positive green shoots were identified at about week 4 of regeneration and transferred from WPM regeneration medium to trays containing Oasis® Wedge System (Smithers-Oasis USA; Kent, Ohio) and a simplified liquid medium (0.5 g/L WPM with 0.25 mg/L IBA). Rooted and shooted R₀ plants were obtained two to 4 weeks later. Overall, pre-culturing in these studies also improved TF % (Table 31). Percentage quality events shown below (Table 22) refers to the proportion of transgenic events demonstrating the presence of 1-2 copies of both a gene of interest (GUS) and a marker gene (aadA) by Invader™ assay. Estimated marker-free TF (mTF) refers the % of events without the marker gene.

TABLE 31

Transformation frequency and quality observed from whole regenerated explants.

| Protocol & vector type | # Explants | # Events produced | TF % | # Events assayed | % quality events | qTF % | Estimated mTF %** |
|---|---|---|---|---|---|---|---|
| Dry Excised-2T/OriV | 260 | 34 | 13.1 +/- 0.17 | 32 | 21.9 | 2.7 +/- 0.23 | 0.62 |

TABLE 31-continued

Transformation frequency and quality observed from whole regenerated explants.

| Protocol & vector type | # Explants | # Events produced | TF % | # Events assayed | % quality events | qTF % | Estimated mTF %** |
|---|---|---|---|---|---|---|---|
| Dry Excised-2T/OriRi | 161 | 15 | 9.32 +/− 7.38 | 14 | 28.6 | 2.5 | 0.45 |
| Pre-cultured Dry-2T/OriV | 1641 | 319 | 19.4 +/− 5.42 | 311 | 24.4 | 4.6 +/− 1.35 | 1.1 |
| Pre-cultured Dry-2T/OriRi | 336 | 66 | 19.64 +/− 1.97 | 64 | 20.3 | 3.9 +/− 1.22 | 0.7 |

Example 17

Production of Transgenic Soybean Plants Using Stored Dry Soybean Embryos, Spectinomycin, and Transfer of Whole Regenerated Explant with a Pre-Culturing Step In this example, 3 months stored dry explants were used, and a 1 hr hydration step done in INO was utilized, on dry excised explant. Pre-culturing was performed for 5 days at 23° C. in dark conditions in BGM with 50 ppm nystatin and 10 ppm TBZ fungicides. TDZ and lipoic acid were both added to the inoculum and to the co-culture media (INO). The construct, pMON107379, was a conventional 2T vector comprising oriRi and aadA gene, and co-culture was done for 5 days. After co-culture the explants were surface plated on solid WPM and then transferred to the Oasis® Wedge System (Smithers-Oasis USA; Kent, Ohio) with a simplified liquid medium (0.5 g/L WPM with 0.25 mg/L IBA). As shown in Table 32, pre-culturing dry explants boosted TF. Thus, 3 month old stored dry explants could perform similarly to freshly excised dry explants. Further, the addition to INO Co-culture media of nystatin (50 ppm) and thiabendazole (10 ppm) dissolved in DMSO (1.0 ml of DMSO per liter of INO) improved the health of explants, likely by controlling yeasts and fungi commonly found in and on seeds and can be a useful tool when performing large and/or automated tissue culture.

TABLE 32

Effect of pre-culture on TF (%) of stored dry explants.

| Explant type | Pre-culture step | # Explants | R0 plants | TF |
|---|---|---|---|---|
| Wet Excised | No | 263 | 75 | 28.52% |
| Stored Dry Explants | No | 678 | 71 | 10.47% |
| Fresh Dry Explants | No | 375 | 24 | 6.40% |
| Stored Dry Explants | Yes | 901 | 129 | 14.32% |
| Fresh Dry Explants | Yes | 1008 | 112 | 11.11% |

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. Nos. 4,761,373; 4,810,648; 5,013,659; 5,015,580; 5,073,675; 5,094,945; 5,141,870; 5,164,310; 5,217,902; 5,229,114; 5,273,894; 5,276,268; 5,322,938; 5,352,605; 5,359,142; 5,362,865; 5,378,824; 5,463,175; 5,512,466; 5,512,466; 5,538,880; 5,543,576; 5,550,318; 5,561,236; 5,563,055; 5,591,616; 5,605,011; 5,608,149; 5,627,061; 5,633,435; 5,633,437; 5,637,489; 5,646,024; 5,689,041; 5,693,512; 5,731,179; 5,750,876; 5,767,366; 5,824,877; 5,850,019; 5,869,720; 5,914,451; 5,958,745; 5,981,834; 5,981,840; 5,985,605; 5,998,700; 6,011,199; 6,040,497; 6,072,103; 6,080,560; 6,140,075; 6,166,292; 6,171,640; 6,225,105; 6,228,623; 6,265,638; 6,271,443; 6,380,462; 6,380,466; 6,384,301; 6,414,222; 6,426,447; 6,444,876; 6,459,018; 6,476,295; 6,483,008; 6,489,461; 6,495,739; 6,531,648; 6,537,750; 6,538,178; 6,538,179; 6,538,181; 6,541,259; 6,576,818; 6,589,767; 6,596,538; 6,613,963; 6,653,530; 6,660,849; 6,706,950; 6,723,837; 6,770,465; 6,774,283; 6,812,379; 6,822,141; 7,022,896; 6,828,475; 5,106,739; 5,378,619; 5,530,196; 5,641,876; 5,659,122; 5,837,848; 6,051,753; 6,140,078; 6,175,060; 6,177,611; 6,232,526; 6,252,138; 6,294,714; 6,426,446; 6,429,357; 6,429,362; 6,433,252; 6,437,217; 6,635,806; 7,002,058; 7,288,694.
U.S. Pat. RE37,543
U.S. Patent Application Publication 2005/0005321; U.S. Patent Application Publication 2006/0059589; U.S. Patent Application Publication 2003/0028917; U.S. Patent Application Publication 2003/0083480; U.S. Patent Application Publication 2003/0115626; U.S. Patent Application Publication 2003/0135879; U.S. Patent Application Publication 2003/110532; U.S. Patent Application Publication 2004/0177399; US Patent Application Publication No. 2004/0244075; U.S. Patent Application Publication 2005/0183170; U.S. Patent Application Publication 2005/0022261; U.S. Patent Application Publication 2006/0200878; U.S. Patent Application Publication 2007/0271627.
Bevan et al., *Nature*, 304:184-187, 1983
Broothaerts et al., *Nature* 433:629-633, 2005.
Callis et al., *Plant Physiol.*, 88:965-968, 1988.
Carrington and Freed, *J. Virology*, 64:1590, 1990.
Chai et al., *Seed Science Research* 8 (Supplement 1):23-28, 1998.

Chandler et al., *Plant Cell,* 1:1175-1183, 1989
Chu et al., *Sci. Sinica* 18:659-668, 1975.
Chu et al., *Scientia Sinica,* 18:659-668, 1975.
Coruzzi et al., *EMBO J.,* 3:1671-1679, 1984.
Daley et al., *Plant Cell Reports* 17:489-496 1998.
Dekeyser et al., *Pl. Physiol.,* 90:217-223, 1989.
Della-Cioppa et al., *Bio/Technology,* 5 579-584, 1987.
Dellaporta et al., In: *Chromosome Structure and Function: Impact of New Concepts,* 18th Stadler Genetics Symposium, 11:263-282, 1988.
Depicker, et al., *J. Mol. Appl. Genet.* 1: 561-574. 1982.
Duncan et al., *Planta* 165:322-332, 1985.s
Elliot et al., *Plant cell Rep.,* 18:707-714, 1999.
EP 0385 962
EP 275,957
Fraley et al., *Proc. Natl. Acad. Sci. USA,* 80:4803-4807, 1983.
Gamborg et al., *Exp Cell Res.* 50:151-8, 1968.
Ikatu et al., *Bio/Technol.,* 8:241-242, 1990.
Jefferson et al., *Biochem. Soc. Trans.,* 15:7-19, 1987a.
Jefferson et al., *EMBO J.,* 6:3901-3907, 1987b.
Katz et al., *J. Gen. Microbiol.,* 129:2703-2714, 1983.
Keller et al., *Transgenic Res.* 6:385-392, 1997.
Klee et al., *Mol. Gen. Genet.,* 210:437-442, 1987.
Komari et al., *Plant J.* 10:165-174, 1996.
Kuhlemeier et al., *Plant Cell,* 1:471-478, 1989.
Lawton et al., *Plant Mol. Biol.* 9:315-324, 1987.
Linsmaier and Skoog, *Physiol. Plant.* 18: 100-127, 1965.
Linsmaier and Skoog, *Physiol. Plant.,* 18 100, 1965.
Lloyd and McCown, *Proc.—Int. Plant Propagator's Soc.,* 30: 421-427, 1981
Marcotte et al., *Plant Cell,* 1:969-976, 1989.
McCabe & Martinell, *Bio/Technology* 11:596-598, 1993.
Miki and McHugh, *J. Biotechnol.,* 107:193-232, 2004.
Miki et al., In: *Methods in Plant Molecular Biology and Biotechnology,* Glick and Thompson ((Eds.), CRC Press, Inc., Boca Raton, pages 67-88, 1993.
Murashige and Skoog, *Physiol. Plant.* 15: 473-497, 1962.
Nitsch and Nitsch, *Science* 163:85-87 1969.
Odell et al., *Nature* 313:810-812, 1985.
Oreifig et al., *Pl. Cell. Rep.* 22:490-496, 2004.
Ow et al., *Science,* 234:856-859, 1986.
PCT Appln. WO 04009761
PCT Appln. WO 04074443
PCT Appln. WO 05003362
PCT Appln. WO 8704181A
PCT Appln. WO8900193A
PCT Appln. WO 00/18939
PCT Appln. WO9215675
PCT Appln. WO9215775
PCT Appln. WO9927116
Sandvang, *Antimicrob. Agents Chemotherapy* 43:3036-3038, 1999.
Senaratna et al., *Pl. Physiol.* 72:620-624, 1983.
Schaffner et al., *Plant Cell,* 3:997-1012, 1991
Schenk and Hildebrandt, *Can. J. Bot.* 50:199-204, 1972.
Sutcliffe et al., *Proc. Natl. Acad. Sci. USA,* 75:3737-3741, 1978.
Svab et al., *Plant Mol. Biol.* 14:197-205, 1990.
Tegeder et al. *Pl. Cell Rep.* 15:164-169, 1995.
Uchimiya and Murashige, *Plant Physiol.* 15:73, 1962.
Uchimiya and Murashige, *Plant Physiol.* 57: 424-429, 1976.
Vertucci and Roos, *Pl. Physiol.* 90:1019-1023, 1990.
Walker et al., *Proc. Natl. Acad. Sci. USA,* 84:6624, 1987
Wuni et al., *Plant Cell,* 1:961-968, 1989.
Yang et al. *Proc. Natl. Acad. Sci. USA,* 87:4144-4148, 1990.
Zambre et al., *Planta* 216:580-586, 2003.
Zukowsky et al., *Proc. Natl. Acad. Sci. USA,* 80:1101-1105, 1983.

What is claimed is:

1. A method of producing a transgenic plant comprising:
   (a) preparing a dry meristematic explant from a dry plant seed,
   (b) pre-culturing the dry meristematic explant prior to transformation in a liquid medium composition for 1-5 days; and
   (c) transforming the explant with a heterologous nucleic acid sequence to produce transformed cells comprising the heterologous nucleic acid sequence.

2. The method of claim 1, wherein the pre-culturing occurs at a temperature of between 23° C. and 28° C.

3. The method of claim 1, wherein pre-culturing occurs in dark conditions.

4. The method of claim 1, wherein the heterologous nucleic acid sequence comprises a selectable marker conferring tolerance to spectinomycin and the explant is contacted, prior to, concurrently with, and/or following step (a) or step (b), with at least a first media comprising spectinomycin to select transformed cells comprising the heterologous nucleic acid sequence.

5. The method of claim 1, wherein the heterologous nucleic acid sequence comprises a selectable marker conferring tolerance to glyphosate.

6. The method of claim 1, wherein the explants are grown in the presence of a fungicide during, or subsequent to step (a).

7. The method of claim 1, further comprising regenerating a transgenic plant from the transformed cells.

8. The method of claim 7, wherein regenerating is performed in liquid regeneration medium.

9. The method of claim 1, wherein the dry explant was stored prior to pre-culturing for a period of time of 3 months to 2 years.

10. The method of claim 1, wherein the dry meristematic explant is prepared under conditions wherein the dry meristematic explant does not germinate and remains viable and competent for genetic transformation.

11. The method of claim 1, further comprising the step of:
 (d) regenerating a transgenic plant from said transformed cells, wherein the plant is stably transformed with the heterologous nucleic acid sequence.

12. The method of claim 1, wherein the dry meristematic explant is stored prior to step (b) under conditions wherein the dry meristematic explant does not germinate.

13. The method of claim 12, wherein the dry meristematic explant is stored at a temperature of between about −80° C. and about 60° C.

14. The method of claim 12, wherein storing the dry meristematic explant is carried out for from about 1 hour to about 24 hours.

15. The method of claim 1, wherein the dry meristematic explant is a soybean, corn, cotton, or canola explant.

16. The method of claim 1, wherein one or more of steps (a), (b) and (c) are automated.

17. The method of claim 11, wherein one or more of steps (a), (b), (c) and (d) are automated.

18. The method of claim 11, wherein the transgenic plant is regenerated without producing a callus cell culture.

19. The method of claim 1, wherein the plant seed from which the explant is prepared comprises an internal moisture content of from about 3% to about 25%.

20. The method of claim 19, wherein the plant seed from which the explant is prepared comprises an internal moisture content of from about 4% to about 16%.

21. The method of claim 1, wherein the explant comprises an internal moisture content of from about 3% to about 25%.

22. The method of claim 21, wherein the explant comprises an internal moisture content of from about 3% to about 16%.

\* \* \* \* \*